United States Patent [19]

Hogen-Esch et al.

[11] Patent Number: 6,143,847
[45] Date of Patent: *Nov. 7, 2000

[54] METHOD FOR PREPARING (CO) POLYMERS BY METAL-FREE ANIONIC POLYMERIZATION IN THE PRESENCE OF A PHOSPHONIUM CATION CONTAINING AT LEAST ONE ANNELLATED AROMATIC RING

[75] Inventors: Thieo E. Hogen-Esch, South Pasadena; Dimo K. Dimov, Los Angeles, both of Calif.; Stephan Jüngling, Mannheim, Germany; Volker Warzelhan, Weisenheim, Germany; Hermann Gausepohl, Mutterstadt, Germany

[73] Assignee: BASF Aktiengesellschaft, Ludwigschafen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/827,906

[22] Filed: Apr. 7, 1997
[51] Int. Cl.[7] .................................................. C08F 2/00
[52] U.S. Cl. ........................................ 526/193; 526/179
[58] Field of Search ..................................... 526/193, 179

[56] References Cited

U.S. PATENT DOCUMENTS 5,610,248   3/1997   Hogen-Esch ........................... 526/193

*Primary Examiner*—Fred Zitomer
*Attorney, Agent, or Firm*—Keil & Weinkauf

[57] ABSTRACT

The present invention concerns a novel method for preparing polymers (preferably (meth)acrylate polymers and copolymers) having a narrow molecular weight distribution by metal-free anionic polymerization in the presence of a phosphonium cation containing at least one annellated aromatic ring as substituent on the phosphorous atom.

11 Claims, No Drawings

METHOD FOR PREPARING (CO) POLYMERS BY METAL-FREE ANIONIC POLYMERIZATION IN THE PRESENCE OF A PHOSPHONIUM CATION CONTAINING AT LEAST ONE ANNELLATED AROMATIC RING

BACKGROUND OF THE INVENTION

1. Field of the Invention

The present invention concerns a novel method for preparing polymers (preferably (meth)acrylate polymers and copolymers) having a narrow molecular weight distribution by metal-free anionic polymerization in the presence of a phosphonium cation containing at least one annellated aromatic ring as substituent on the phosphorous atom.

2. Discussion of the Background

In the last decade, great interest has emerged concerning the polymerization of (meth)acrylates, particularly methyl methacrylate (MMA), under ambient conditions. A number of new polymerization systems have been reported, and a recent review covers most of the literature on the polymerization of MMA at ambient temperatures (T. P. Davis, D. M. T. Haddelton, S. N. Richards, J. M. S.-Rev. Macromol. Chem Phys, 1994, C34, 243).

For example, a process known as Group Transfer Polymerization (GTP), introduced in the early 1980's, produced poly(methyl methacrylate) (PMMA) and allowed control of molecular weight distribution (MWD), molecular weight and molecular architecture at ambient temperatures (Webster et al. J. Am Chem. Soc. 1983, 105, 5706).

Reetz et al (Angew. Chem. Int. Ed. Engl. 1988, 27, 1371; Polymer Preprints (Am. Chem. Soc., Div. Polym. Chem.) 1991, 32, 296) have postulated that, in the anionic polymerization of n-butyl acrylate at ambient temperatures using a tetrabutylammonium countercation, the intramolecular Claisen type termination reaction is decreased because the electrostatic attraction between the alkoxide and the bulky n-Bu$_4$N$^+$ cation is weak, thereby thermodynamically and kinetically disfavoring the formation of the termination by-product tetrabutylammonium alkoxide. However, anionic polymerizations with ammonium countercations also suffer from some drawbacks, such as low yield, which may be the result of a Hoffmann elimination of a β-hydrogen from the ammonium cation at a rate competitive with polymerization.

A distinct improvement on the methods described is constituted by the anionic polymerization in the presence of phosphonium counterions (WO 96/28487, U.S. patent application Ser. No. 08/609,732). According to WO 96/28487 the polymerization is carried out at temperatures of up to 40° C.

The polymerization of acrylic acid derivatives at temperatures of more than 20° C. and particularly between 40 and 120° C. in the presence of an initiator corresponding to or containing the structure

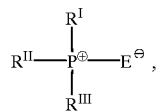

(V)

where E may be CR$^{IV}$R$^V$ and where C together with R$^{IV}$ and R$^V$ may form an unsaturated isocyclic ring was disclosed in DE-A 36 32 361 and DE-A 37 00 195. Since a phosphonium species is found to be covalently linked to the polymer chain formed a mechanism according to Klippert and Ringsdorf (Makromol. Chem. 1972, 53, 289–306) where the ylide carbon atom attacks the acrylic or methacrylic monomer can be postulated. The initiator (V) can also be used in its protonated form. As shown in the examples the best results are obtained when the initiator is employed as Lewis acid adduct. Merely very poor yields, incomplete monomer conversion and polymers having a broad molecular weight distribution are obtained when the reaction is performed in the presence of the neutral catalyst. In the case of the protonated species the acidic proton may cause chain termination. Therefore, the scope of the polymerization using (V) is limited.

Another entry to metal-free anionic polymerization of acrylates and methacrylates disclosed by Seebach and Pietzonka (Angew. Chem. Int. Ed. Engl. 1993, 32, 716) makes use of the P4-phosphazene base introduced by Schwesinger and Schlemper (Angew. Chem. 1987, 99, 1212) which forms a very soft and bulky cation. The initiating system can for example be prepared by treating ethyl acetate with the P4-phosphazene base. Polymerization of for example methylmethacrylate is accomplished at 60° C. furnishing predominantly a syndiotatic polymer material. However, the P4-phosphazene base is not readily available and therefore not favorable for large scale production. In addition, the formation of block copolymers has not yet been disclosed.

Thus, a need exists for a method for producing poly(meth)acrylate polymers and copolymers having a narrow molecular weight distribution, which provides effective control of (co)polymer molecular weight, of molecular weight distribution and of (co)polymer stereoregularity in good yields and at technically favorable temperatures, also allowing for large scale production.

OBJECTS OF THE INVENTION

Accordingly, it is one object of the present invention to provide a novel method for anionically producing (co) polymers which provides a (co)polymer having a narrow molecular weight distribution.

It is a further object of the present invention to provide a novel method for producing (co)polymers by anionic polymerization which provides effective control of (co)polymer molecular weight.

It is a further object of the present invention to provide a novel method for producing (co)polymers by anionic polymerization which provides the (co)polymer in good yields.

It is a further object of the present invention to provide a novel method for producing (co)polymers which achieves the above objects in a controlled manner at temperatures higher than 40° C. and in particular at temperatures higher than 60° C.

It is a further object of the present invention to provide a novel initiator for producing (co)polymers by anionic polymerization.

Furthermore, it is one object of the present invention to provide a novel method for anionically producing poly (meth)acrylate (co)polymers which provides a (co)polymer having a narrow molecular weight distribution.

It is a further object of the present invention to provide a novel method for producing poly(meth)acrylate (co) polymers by anionic polymerization which provides effective control of (co)polymer molecular weight.

It is a further object of the present invention to provide a novel method for producing poly(meth)acrylate (co) polymers by anionic polymerization which can provide effective control of (co)polymer stereoregularity (e.g. syndiotacticity).

It is a further object of the present invention to provide a novel method for producing poly(meth)acrylate (co)polymers by anionic polymerization which provides the (co)polymer in good yields.

It is a further object of the present invention to provide a novel method for producing poly(meth)acrylate (co)polymers which achieves the above objects in a controlled manner at temperatures higher than 40° C. and in particular at temperatures higher than 60° C.

It is a further object of the present invention to provide a novel initiator for producing poly(meth)acrylate (co)polymers by anionic polymerization.

These and other objects, which will become apparent in the following detailed description of the preferred embodiments, have been provided by a method for producing a (co)polymer, particularly a (meth)acrylate (co)polymer, which comprises:

mixing a monomer of the formula I, or a monomer of the formula II, or a mixture of both I and II:

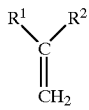

(I)

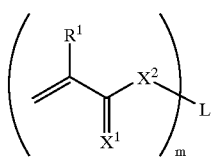

(II)

with an initiator corresponding to or containing

[(R$^6$R$^7$R$^8$PR$^9$)$^+$]$_n$ Q$^{n-}$ (III) and/or (R$^6$R$^7$R$^8$PR$^9$)$^+$ (Q')$^-$ (IV)

and conducting the reaction at a temperature of from more than 40° C., in the presence or the absence of a solvent, for a length of time sufficient to polymerize the monomer(s) and to form a (co)polymer; and isolating the formed (co)polymer, wherein:

R$^1$ is selected from the group consisting of H, CN, CF$_3$, alkyl of from 1 to 6 carbon atoms and C$_6$- to C$_{18}$-aryl, R$^2$ is independently selected from the group consisting of CN, C(=X$^1$)R$^3$, C(=X$^1$)NR$^4$R$^5$ and heterocyclic rings capable of stabilizing an α-anion, X$^1$ is iminoalkyl of from 1 to 20 carbon atoms, iminoaryl of from 6 to 18 carbon atoms, O or S, R$^3$ is alkyl of from 1 to 20 carbon atoms, substituted alkyl of from 1 to 20 carbon atoms having as substituents one or more halides, —O-alkyl of from 1 to 20 carbon atoms, substituted
—O-alkyl of from 1 to 20 carbon atoms having as substituents one or more halides,
—O-alkyl of from 3 to 20 carbon atoms having one or more epoxy units,
—O-cycloalkyl of from 3 to 15 carbon atoms,
—O-cycloalkyl of from 3 to 15 carbon atoms having as substituents one or more halides,
—O-cycloalkyl of from 5 to 12 carbon atoms having one or more epoxy units,
—O-alkenyl of from 2 to 12 carbon atoms,
—O—R'—O—R" or —O—R'—NR"R"', wherein R' is an alkylene chain of from 2 to 10 carbon atoms, C$_6$- to C$_{18}$-arylene, an alkylene chain having one or more ether units in the chain, R" is C$_1$- to C$_{10}$-alkyl, C$_6$- to C$_{18}$-aryl, C$_3$- to C$_{10}$-cycloalkyl, or C$_3$- to C$_{30}$-organosilyl and R'" is H, C$_1$- to C$_{10}$-alkyl, C$_6$- to C$_{18}$-aryl, C$_3$- to C$_{10}$-cycloalkyl, C$_3$- to C$_{30}$-organosilyl, or —S-alkyl of from 1 to 20 carbon atoms;

R$^4$ and R$^5$ are independently alkyl of from 1 to 20 carbon atoms, alkyl of from 1 to 20 carbon atoms having as substituents one or more halides, or are joined together to form an alkylene ring of from 2 to 8 carbon atoms or an alkylene ring of from 2 to 8 carbon atoms containing one or more additional heteroatoms, selected from the group consisting of the elements of group VA and VIA of the periodic table of the elements, thus forming a 3- to 10-membered ring, cycloalkyl of from 3 to 12 carbon atoms, or alkenyl of from 2 to 12 carbon atoms;

X$^2$ is aminoalkyl of from 1 to 20 carbon atoms, aminoaryl of from 6 to 18 carbon atoms, O, S S or —C(R$^a$)(R$^b$)—, wherein R$^a$ and R$^b$ are independently H, C$_1$- to C$_{20}$-alkyl, C$_3$- to C$_{12}$-cycloalkyl or C$_6$- to C$_{18}$-aryl, L is an organic radical of value m, m is an integer of from 2 to 20;

R$^6$, R$^7$ and R$^8$ are independently C$_6$- to C$_{22}$-aryl or substituted C$_6$- to C$_{22}$-aryl having one or more substituents selected from the group consisting of alkyl of from 1 to 20 carbon atoms, oxyalkyl of from 1 to 20 carbon atoms, C$_6$- to C$_{22}$-aryl, substituted C$_6$- to C$_{22}$-aryl, oxy-C$_6$- to C$_{22}$-aryl, substituted oxy-C$_6$- to C$_{22}$-aryl, alkylene-oxy-alkyl of from 2 to 20 carbon atoms, aminodialkyl of from 2 to 30 carbon atoms, amino(alkyl)(aryl) of from 7 to 30 carbon atoms, aminodiaryl of from 12 to 36 carbon atoms, halides, thio-alkyl of from 1 to 20 carbon atoms, thio-C$_6$- to C$_{22}$-aryl, and substituted thio-C$_6$- to C$_{22}$-aryl, R$^9$ is C$_{10}$- to C$_{22}$-aryl or substituted C$_{10}$- to C$_{22}$-aryl having one or more substituents selected from the group consisting of alkyl of from 1 to 20 carbon atoms, oxyalkyl of from 1 to 20 carbon atoms, C$_6$- to C$_{22}$-aryl, substituted C$_6$- to C$_{22}$-aryl, oxy-aryl of from 6 to 22 carbon atoms, substituted oxy-aryl of from 6 to 22 carbon atoms, alkylene-oxy-alkyl of from 2 to 20 carbon atoms, aminodialkyl of from 2 to 30 carbon atoms, amino(alkyl)(aryl) of from 7 to 30 carbon atoms, aminodiaryl of from 12 to 36 carbon atoms, halides, thio-alkyl of from 1 to 20 carbon atoms, thio-C$_6$- to C$_{22}$-aryl, and substituted thio-C$_6$- to C$_{22}$-aryl, Q is CR$^{10}$R$^{11}$R$^{12}$, NR$^{13}$R$^{14}$, OR$^{15}$, SR$^{16}$ or R$^{17}$(CR$^{10}$R$^{11}$)$_p$(NR$^{13}$)$_q$(O)$_r$(S)$_s$ wherein p, q, r and s are independently an integer of from 0 to 30 and where the sum of p to s is at least 2;

Q' is R$^{18}$—CR$^{10}$R$^{11}$R$^{12}$, R$^{18}$—NR$^{13}$R$^{14}$, R$^{18}$—OR$^{15}$, R$^{18}$—SR$^{16}$, R$^{18}$—Z;

R$^{10}$ and R$^{11}$ are independently alkyl, each of from 1 to 20 carbon atoms, alkyl of from 1 to 20 carbon atoms having as substituents one or more halides, C$_6$- to C$_{18}$-aryl, substituted C$_6$- to C$_{18}$-aryl, CN, C(=X$^1$)R$^3$ as defined above, C(=X$^1$)NR$^4$R$^5$ as defined above, organosilyl having from 3 to 30 carbon atoms, or either R$^{10}$ or R$^{11}$ are H, or R$^{10}$ and R$^{11}$ are joined together to form a ring, having from 3 to 10 carbon atoms, R$^{12}$ is H, alkyl of from 1 to 20 carbon atoms, C$_6$- to C$_{18}$-aryl, or a (co)polymer radical;

R$^{13}$ and R$^{14}$ are independently alkyl of from 1 to 20 carbon atoms, C$_6$- to C$_{18}$-aryl, C$_7$- to C$_{20}$ aralkyl, C$_3$- to $C_{30}$-organosilyl, $C(=X^1)R^3$ as defined above, or $R^{13}$ and $R^{14}$ are joined together to form a heterocycle, $R^{15}$ and $R^{16}$ are independently alkyl of from 1 to 20 carbon atoms, cycloalkyl of from 3 to 10 carbon atoms or $C_6$- to $C_{18}$-aryl, $R^{17}$ is an organic radical of value n, $R^{18}$ is a (co)polymer radical, Z is a radical derived from an initiator for the anionic polymerization of anionic polymerizable monomers other than radicals derived from compounds III or IV and n is an integer of from 1 to 30.

DETAILED DESCRIPTION OF THE PREFERRED EMBODIMENTS

The present process can be used to make polymers and copolymers (statistical copolymers as well as block copolymers) (hereinafter "(co)polymers") from a wide variety of monomers. Vinyl monomers suitable for the present process should preferably bear at least one electron-withdrawing and/or formal negative charge-stabilizing group, such as an ester group, a keto group, a sulfone group, a phosphonate group, a heterocyclic ring, etc. In the context of the present invention both acrylates and methacrylates fall under the definition of the term (meth)acrylates. The initiator can comprise any stabilized carbanion, but preferably one in which the corresponding neutral carbon acid has a PKa of from 12 to 37, and more preferably, a PKa of from 18 to 35. Alternatively the initiator can comprise amide anions, oxide anions or sulfide anions. It is within the scope of the present invention that mixtures of different anions may be used as well. The key to the present process involving the anionic, metal-free polymerization of a vinyl monomer lies in the use of a phosphonium countercation containing at least one annellated aromatic ring as substituent on the phosphorous atom. In the context of this invention the term initiator encompasses also mixtures of two or more different initiators.

The present invention provides (co)polymers, and particularly poly(meth)acrylates, having a relatively narrow molecular weight distribution, in quantitative or nearly quantitative yields at reaction temperatures higher than 40° C. Molecular weights of the (co)polymers produced by the present process, which may be weight average or number average molecular weights, may be controlled by controlling the molar ratio of initiator to monomer, and may range from 500 g/mol to 300,000 g/mol, preferably from 1,000 to 200,000 g/mol, and most preferably from 2,000 to 100,000 g/mol. Even at 70° C. the (co)polymers produced exhibit a narrow molecular weight distribution ($M_w/M_n \leq 1.2$) (e.g., a $M_w/M_n$ of about 1.18 for a PMMA produced using [(1-Naphthyl)P(Ph)$_3$]$^+$(CPh$_3$)$^-$ (Ph denoting phenyl), having a $M_n$ of 19,000 g/mol). In the context of the present application, a narrow molecular weight distribution refers to a (co)polymer having an average molecular weight distribution ($M_w/M_n$) of $\leq 2.0$, preferably $\leq 1.5$, and most preferably $\leq 1.2$.

The polymerization rate of the present method is relatively moderate over a very wide temperature range, allowing for a control of reaction conditions and product parameters. Monomer conversions typically are complete (e.g., at least 90%, preferably at least 95% and most preferably at least 98% of the monomer are consumed during the polymerization reaction).

Because the present reacting step is a "living" polymerization, the process can be applied to the preparation of block and multi-block copolymers. The bulky phosphonium cations are believed to prevent intramolecular cation coordination to the ante-penultimate ester carbonyl group.

Polymers produced using the present process have a variety of uses. For example, PMMA is the polymer used to make transparent molds such as glaslike sheets. Furthermore, the polymers produced by the present method have sufficiently narrow molecular weight distributions as to provide PMMA or other polymer standards for size exclusion chromatography.

Monomers suitable for polymerization in the present method include those of the formula (I):

(I)

wherein $R^1$ is selected from the group consisting of H, CN, $CF_3$, alkyl which can be linear, branched or cyclic of from 1 to 6 carbon atoms such as methyl, ethyl, n-propyl, i-propyl or cyclohexyl and $C_6$- to $C_{18}$-aryl, in particular H, methyl or phenyl, $R^2$ is independently selected from the group consisting of CN, $C(=X^1)R^3$, $C(=X^1)NR^4R^5$ and heterocyclic rings capable of stabilizing an α-anion, in particular $C(=O)R^3$, $X^1$ is iminoalkyl which can be linear, branched or cyclic of from 1 to 20 carbon atoms, in particular of from 1 to 10 carbon atoms, such as methyl, ethyl, n-propyl, i-propyl or cyclohexyl, iminoaryl of from 6 to 18 carbon atoms, in particular of from 6 to 10 carbon atoms, such as phenyl, O or S, in particular O, $R^3$ is alkyl which can be linear, branched or cyclic of from 1 to 20 carbon atoms, in particular of from 1 to 10 carbon atoms, such as methyl, ethyl, n-propyl, i-propyl or cyclohexyl, substituted alkyl of from 1 to 20 carbon atoms having as substituents one or more halides, such as fluorine or chlorine, e.g. trifluoromethyl or pentafluoroethyl, —O-alkyl of from 1 to 20 carbon atoms, such as methyl, ethyl, n-propyl, i-propyl, n-butyl, i-butyl, t-butyl, n-pentyl, i-pentyl, n-hexyl, n-heptyl, n-octyl, n-nonyl, n-decyl, n-dodecyl, n-tetradecyl, n-hexadecyl, n-octadecyl, n-eicosyl, 2-methylpropyl, 2-methylbutyl, 2-methylhexyl, 2-methyloctyl, 2-ethylbutyl, 2-ethylpentyl, 2-ethylhexyl, 2-ethyloctyl, 3-methylbutyl, 3-methylpentyl, 3-methylhexyl, 3-methyloctyl, 3-ethylpentyl, 3-ethylhexyl, 3-ethyloctyl, wherein methyl, n-butyl, t-butyl, 2-ethylhexyl and n-dodecyl are particularly preferred, substituted —O-alkyl which can be linear or branched of from 1 to 20 carbon atoms, in particular of from 1 to 10 carbon atoms, having as substituents one or more $C_6$- to $C_{18}$-aryl groups, such as 2-phenylethyl, 2-phenyl-n-propyl, 2-phenyl-n-butyl, 2-phenyl-n-pentyl, 2-phenyl-n-hexyl or 2-phenyl-n-octyl, substituted —O-alkyl which can be linear or branched of from 1 to 20 carbon atoms, in particular of from 1 to 10 carbon chlorine atoms, having as substituents one or more halides, such as chlorine or fluorine, in particular those of from 1 to 6 carbon atoms, such as trifluoromethyl, pentafluoroethyl or 2,2,2-trifluoroethyl, —O-alkyl which can be linear or branched of from 3 to 20 carbon atoms having one or more epoxy units, in particular those having 1 to 10 carbon atoms, such as O—(2,3-epoxy-1-propyl), —O-cycloalkyl of from 3 to 15 carbon atoms, in particular of from 3 to 12 carbon atoms, such as cyclohexyl, 4-t-butylcyclohexyl or i-bornyl, —O-cycloalkyl of from 3 to 15 carbon atoms having as substituents one or more halides, such as chlorine or fluorine, in particular of from 5 to 12 carbon atoms, such as 2-chlorocyclohexane, —O-cycloalkyl of from 3 to 12 carbon atoms having one or more epoxy units, such as 2,3-epoxycyclohexane, —O-alkenyl of from 2 to 12 carbon atoms, in particular of from 3 to 10 carbon atoms, such as —O-allyl or —O-dihydrodicyclopentadienyl, —O—R'—O—R" or —O—R'—NR"R'", wherein R' is an alkylene chain which can be linear, branched or cyclic of from 1 to 10 carbon atoms, in particular of from 2 to 4 carbon atoms, such as ethylene 1,2-propylene, 1,3-propylene or 1,4-butylene, $C_6$- to $C_{18}$-arylene, in particular o-, m- or p-phenylene, an alkylene chain having one or more ether units in the chain, such as —(CH$_2$CH$_2$O)$_{1\ to\ 5}$(CH$_2$CH$_2$)—, in particular 1 to 3 ether units, R" is $C_1$- to $C_{10}$-alkyl, which can be linear or branched in particular $C_1$- to $C_6$-alkyl, such as methyl, ethyl, n-propyl, i-propyl or n-butyl, $C_6$- to $C_{18}$-aryl, in particular $C_6$- to $C_{10}$-aryl, such as phenyl, $C_3$- to $C_{10}$-cycloalkyl, in particular $C_3$- to $C_6$-cycloalkyl, such as cyclohexyl, or $C_3$- to $C_{30}$-organosilyl, in particular $C_3$- to $C_{18}$-organosilyl in which the tetravalent silicon atom is preferably substituted with radicals selected from the group consisting of alkyl which can be linear, branched or cyclic having from 1 to 20 carbon atoms, in particular of from 1 to 10 carbon atoms, such as methyl, ethyl, i-propyl, n-butyl, t-butyl or cyclohexyl, aryl having from 6 to 18 carbon atoms, in particular of from 6 to 10 carbon atoms, such as phenyl, and aralkyl, being formed from a $C_1$- to $C_6$-alkylene moiety, in particular a $C_1$- to $C_3$-alkylene moiety, and a $C_6$- to $C_{18}$-aryl moiety, in particular a $C_6$- to $C_{10}$-aryl moiety, such as benzyl, examples are trimethylsilyl, triethylsilyl, triphenylsilyl, dimethylphenylsilyl or methyldiphenylsilyl, and R'" is H and otherwise as defined above for R", —S-alkyl which can be linear or branched of from 1 to 20 carbon atoms, in particular of from 2 to 12 carbon atoms, such as ethyl, n-propyl, i-propyl, cyclohexyl, n-dodecyl or t-dodecyl;

$R^4$ and $R^5$ are independently alkyl which can be linear or branched of from 1 to 20 carbon atoms, in particular of from 1 to 10 carbon atoms, such as methyl, ethyl, n-propyl, i-propyl or cyclohexyl, alkyl which can be linear or branched of from 1 to 20 carbon atoms having as substituents one or more halides, in particular those of from 1 to 10 carbon atoms, such as fluorine or chlorine, e.g. trifluoromethyl, or are joined together to form an alkylene ring, in particular an alkylene ring of from 2 to 8, preferably from 2 to 5 carbon atoms, such as tetrahydropyrolidin, or an alkylene ring containing one or more additional heteroatoms, selected from the group consisting of the elements of group VA and VIA of the periodic table of the elements, in particular such a ring containing of from 2 to 8 carbon atoms and preferably having an oxygen or nitrogen atom in the ring, such as a morpholino ring, thus forming a 3- to 10-membered ring, cycloalkyl of from 3 to 12 carbon atoms, such as cyclohexyl, or alkenyl of from 2 to 12 carbon atoms, in particular of from 3 to 10 carbon atoms, such as allyl.

More specifically, preferred monomers include acrylate and methacrylate esters of alkanols of from 1 to 20 carbon atoms, in particular of from 1 to 12 carbon atoms, such as methyl acrylate, n-butyl acrylate, t-butyl acrylate, ethyl acrylate, 2-ethylhexyl acrylate, methyl methacrylate, ethyl methacrylate or 2-ethylhexyl methacrylate, n-butyl methacrylate, t-butyl methacrylate, lauryl methacrylate, allyl methacrylate, dicyclopentadienylmethacrylate or acrylonitrile. Preferred monomers are also vinyl heterocycles selected from the group consisting of vinyl pyridines, preferably 2-pyridine or 4-pyridine and vinyl pyrimidines. Also preferred are cyanoacrylate esters of $C_1$- to $C_{20}$-alcohols. The most preferred monomers are methyl methacrylate, 2-ethylhexylacrylate, n-butyl methacrylate, t-butyl methacrylate, lauryl methacrylate, allyl methacrylate, in particular methylmethacrylate (MMA) and t-butylmethacrylate.

Monomers suitable for polymerization in the present method include also those of the formula II

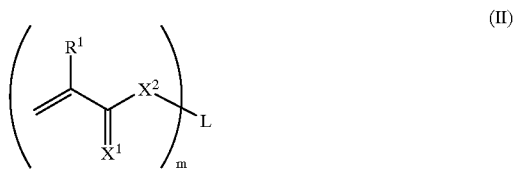

wherein:

$R^1$ and $X^1$ are as defined above;

$X^2$ is aminoalkyl which can be linear, branched or cyclic of from 1 to 20 carbon atoms, in particular of from 1 to 10 carbon 40 atoms, such as methyl, ethyl, n-propyl, i-propyl or cyclohexyl, aminoaryl of from 6 to 18 carbon atoms, preferably phenyl, O, S or —C ($R^a$)($R^b$)—, wherein $R^a$ and $R^b$ are independently H, $C_1$- to $C_{20}$-alkyl which can be linear or branched, preferably $C_1$- to $C_{10}$-alkyl such as methyl, ethyl, n-propyl or i-propyl, $C_3$- to $C_{12}$-cycloalkyl, preferably $C_3$- to $C_6$-cycloalkyl such as cyclohexyl, or $C_6$- to $C_{18}$-aryl, preferably phenyl; O being particularly preferred, L is an organic radical of value m, in particular an aliphatic moiety such as an alkylene of from 1 to 30 carbon atoms, preferably of from 1 to 16 carbon atoms, or an aromatic moiety such as an arylene of from 6 to 18 carbon atoms, which may be substituted with m functional groups CH$_2$=C($R^1$)C(=X$^1$)X$^2$—, as defined above, such as 1,2-ethylene, 1,2-propylene, 1,3-propylene, bisphenylen, pentaerythryl, and m is an integer of from 2 to 20.

More specifically, preferred monomers (II) include di-and polyacrylate esters and di- and polymethacrylate esters derived from di- and polyols having from 2 to 20 carbon atoms, in particular from 2 to 16 carbon atoms, such as ethylene glycol, 1,4-butanediol, pentaerythrit, resorcinol, hydroquinone, brenzcatechinol, polyether units having 2 or more hydroxy groups or glycerol.

In the context of the present invention, with respect to formula (I) and (II), "$C_6$- to $C_{18}$-aryl" preferably refers to phenyl and naphthyl, which may be substituted from 1 to 5 times (in the case of phenyl) or from 1 to 7 times (in the case of naphthyl) and preferably from 1 to 3 times (in both cases) as defined above. Most preferably, "aryl" in (I) or (II) refers to phenyl.

Suitable initiators include those of the formula III:

$$[(R^6R^7R^8PR^9)^+]_n \, Q^{n-} \qquad (III)$$

wherein $R^6$, $R^7$ and $R^8$ are independently $C_6$- to $C_{22}$-aryl, in particular $C_6$- to $C_{14}$-aryl, such as phenyl, naphthyl, fluorenyl, anthracenyl or phenanthryl, or substituted $C_6$- to $C_{22}$-aryl, in particular $C_6$- to $C_{14}$-aryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, n-butyl, i-butyl, t-butyl, n-pentyl, n-hexyl, n-heptyl, n-octyl, n-nonyl, n-decyl, n-undecyl, n-dodecyl, n-hexadecyl, cyclopropyl, cyclopentyl or cyclohexyl; oxyalkyl of from 1 to 20 carbon atoms, in particular of from 1 to 16 carbon atoms, in which alkyl may be linear, branched or cyclic, such as —O-methyl, —O-ethyl, —O-n-propyl, —O-i-propyl, —O-n-butyl, —O-i-butyl, —O-t-butyl, —O-n-pentyl, —O-n-hexyl, —O-n-heptyl, —O-n-octyl, —O-n-nonyl, —O-n-decyl, —O-n-dodecyl, —O-n-hexadecyl, —O-cyclopropyl, —O-cyclopentyl, —O-cyclohexyl, —O—$(CH_2CH_2O)_{1 \, to \, 5}$—$CH_3$; $C_6$- to $C_{22}$-aryl, in particular $C_6$- to $C_{14}$-aryl, such as phenyl; substituted $C_6$- to $C_{22}$-aryl, in particular $C_6$- to $C_{14}$-aryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, t-butyl, n-dodecyl or cyclohexyl; oxy-$C_6$- to $C_{22}$-aryl, in particular oxy-$C_6$- to $C_{14}$-aryl, such as —O-phenyl; substituted oxy-$C_6$- to $C_{22}$-aryl, in particular oxy-$C_6$- to $C_{14}$-aryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, t-butyl, n-dodecyl or cyclohexyl; alkylene-oxy-alkyl of from 2 to 20 carbon atoms, in particular of from 3 to 17 carbon atoms, such as —$(CH_2)_{1 \, to \, 5}$—O—$(CH_2CH_2O)_{0 \, to \, 5}$—$CH_3$; aminodialkyl of from 2 to 30 carbon atoms, in particular of from 2 to 14 carbon atoms, such as dimethylamino, diethylamino, di(n-propyl)amino, di(i-propyl)amino, di(n-butyl)amino, di(i-butyl)amino, (methyl)(ethyl)amino; aminoalkylaryl of from 7 to 30 carbon atoms, in particular of from 7 to 15 carbon atoms, such as (methyl)(phenyl)amino, (ethyl)(phenyl)amino; aminodiaryl of from 12 to 36 carbon atoms, in particular of from 12 to 28 carbon atoms, such as diphenylamino, dinaphthylamino or (naphthyl)(phenyl)amino; halides, in particular fluoride, chloride, bromide or iodide, preferably fluoride, chloride or bromide; thio-alkyl of from 1 to 20 carbon atoms, in particular from 1 to 16 carbon atoms, in which alkyl may be linear, branched or cyclic, such as —S-methyl, —S-ethyl, —S-n-propyl, —S-i-propyl, —S-n-butyl, —S-i-butyl, —S-t-butyl, —S-n-pentyl, —S-n-hexyl, —S-n-heptyl, —S-n-octyl, —S-n-nonyl, —S-n-decyl, —S-n-dodecyl, —S-n-hexadecyl, —S-cyclopropyl, —S-cyclopentyl, —S-cyclohexyl; thio-$C_6$- to $C_{22}$-aryl, in particular thio-$C_6$- to $C_{14}$-aryl, such as phenyl or naphthyl; substituted thio-$C_6$-to $C_{22}$-aryl, in particular thio-$C_6$- to $C_{14}$-aryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, n-butyl, i-butyl, t-butyl, n-dodecyl or cyclohexyl.

The $C_6$- to $C_{22}$-aryl in $R^6$, $R^7$ and $R^8$ may be mono-, di-, poly- or persubstituted with substituents as defined above. Thus, if the aryl moiety is phenyl or naphthyl, phenyl may have from 1 to 5 substituents, naphthyl may have from 1 to 7 substituents, most preferably phenyl or naphthyl may have from 1 to 3 substituents. Longer chain substituents, e.g. C10- to $C_{20}$-alkyl, such as dodecyl, hexadecyl or eicosyl, or —O—$C_{10}$- to $C_{20}$-alkyl, such as —O—dodecyl, —O-hexadecyl or —O-eicosyl, on, for example, the phenyl or the naphthyl may be preferred if it is desired to increase the solubility of the initiator in solvents like for example tetrahydrofurane (THF) or ethylbenzene. Most preferably, each of $R^6$, $R^7$ and $R^8$ is phenyl.

$R^9$ is $C_{10}$- to $C_{22}$-aryl, in particular $C_{10}$- to $C_{14}$-aryl, such as 1-naphthyl, 2-naphthyl, 1-anthracenyl, 2-anthracenyl, 9-anthracenyl, 1-phenanthryl, 2-phenanthryl, 3-phenanthryl, 4-phenanthryl or 9-phenanthryl, or substituted $C_{10}$- to $C_{22}$-aryl, in particular $C_{10}$- to $C_{14}$-aryl, such as 1-naphthyl, 2-naphthyl, 1-anthracenyl, 2-anthracenyl, 9-anthracenyl, 1-phenanthryl, 2-phenanthryl, 3-phenanthryl, 4-phenanthryl or 9-phenanthryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, n-butyl, i-butyl, t-butyl, n-pentyl, n-hexyl, n-heptyl, n-octyl, n-nonyl, n-decyl, n-undecyl, n-dodecyl, n-hexadecyl, cyclopropyl, cyclopentyl or cyclohexyl; oxyalkyl of from 1 to 20 carbon atoms, in particular of from 1 to 16 carbon atoms, in which the alkyl radical may be linear, branched or cyclic, such as —O-methyl, —O-ethyl, —O-n-propyl, —O-i-propyl, —O-n-butyl, —O-i-butyl, —O-t-butyl, —O-n-pentyl, —O-n-hexyl, —O-n-heptyl, —O-n-octyl, —O-n-nonyl, —O-n-decyl, —O-n-dodecyl, —O-n-hexadecyl, —O-cyclopropyl, —O-cyclopentyl, —O-cyclohexyl, —O—$(CH_2CH_2O)_{1 \, to \, 5}$—$CH_3$; $C_6$- to $C_{22}$-aryl, in particular $C_6$- to $C_{14}$-aryl, such as phenyl; substituted $C_6$- to $C_{22}$-aryl, in particular $C_6$- to $C_{14}$-aryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, t-butyl, n-dodecyl or cyclohexyl; oxyaryl of from 6 to 22 carbon atoms, in particular of from 6 to 14 carbon atoms, such as —O-phenyl or —O-naphthyl; substituted oxy-aryl of from 6 to 22 carbon atoms, in particular of from 6 to 14 carbon atoms, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, n-butyl, i-butyl, t-butyl, n-dodecyl or cyclohexyl; alkylene-oxy-alkyl of from 2 to 20 carbon atoms, in particular of from 3 to 17 carbon atoms, such as —$(CH_2)_{1 \, to \, 5}$—O—$(CH_2CH_2O)_{0 \, to \, 5}$—$CH_3$; aminodialkyl of from 2 to 30 carbon atoms, in particular of from 2 to 14 carbon atoms, such as dimethylamino, diethylamino, di(n-propyl)amino, di(i-propyl)amino, di(n-butyl)amino, di(i-butyl)amino, (methyl)(ethyl)amino; amino(alkyl)(aryl) of from 7 to 30 carbon atoms, in particular of from 7 to 15 carbon atoms, such as (methyl)(phenyl)amino, (ethyl)(phenyl)amino; aminodiaryl of from 12 to 36 carbon atoms, in particular of from 12 to 28 carbon atoms, such as diphenylamino, dinaphthylamino or (naphthyl)(phenyl)amino; halides, in particular fluoride, chloride, bromide or iodide, preferably fluoride, chloride or bromide; thio-alkyl of from 1 to 20 carbon atoms, in particular of from 1 to 16 carbon atoms, in which alkyl may be linear, branched or cyclic, such as —S-methyl, —S-ethyl, —S-n-propyl, —S-i-propyl, —S-n-butyl, —S-i-butyl, —S-t-butyl, —S-n-pentyl, —S-n-hexyl, —S-n-heptyl, —S-n-octyl, —S-n-nonyl, —S-n-decyl, —S-n-dodecyl, —S-n-hexadecyl, —S-cyclopropyl, —S-cyclopentyl, —S-cyclohexyl; thio-$C_6$- to $C_{22}$-aryl, in particular thio-$C_6$- to $C_{14}$-aryl, such as thiophenyl; substituted thio-$C_6$- to $C_{22}$-aryl, in particular thio-$C_6$- to $C_{14}$-aryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, n-butyl, i-butyl, t-butyl, n-dodecyl or cyclohexyl.

The $C_6$- to $C_{22}$-aryl in $R^9$ may be mono-, di-, poly- or persubstituted with substituents as defined above. Thus, naphthyl may be substituted or from 1 to 7 times, anthracenyl and phenanthryl of from 1 to 9 times. Preferably naphthyl, anthracenyl or phenanthryl may be substituted of from 1 to 5 times.

Longer chain substituents, e.g. $C_{10}$- to $C_{20}$-alkyl, such as dodecyl, hexadecyl or eicosyl, or —O—$C_{10}$- to —O—$C_{20}$-alkyl, such as —O-dodecyl, —O-dodecyl or —O-eicosyl, on the annellated rings may be preferred if it is desired to increase the solubility of the initiator in solvents like for example tetrahydrofurane (THF), toluene, cyclohexane, dimethoxyethane, ethylbenzene or mixtures thereof. Most preferably, $R^9$ is naphthyl.

Q is $CR^{10}R^{11}R^{12}$, $NR^{13}R^{14}$, $OR^{15}$, $SR^{16}$ or $R^{17}(CR^{10}R^{11})_p(NR^{13})_q(O)_r(S)_s$ wherein p, q, r and s are independently an integer of from 0 to 30 and where the sum of p to s is at least 2;

$R^{10}$ and $R^{11}$ are independently alkyl which may be linear, branched or cyclic of from 1 to 20 carbon atoms, in particular of from 1 to 10 carbon atoms, such as methyl, ethyl, n-propyl, i-propyl, n-butyl, i-butyl, t-butyl, n-pentyl, n-hexyl, n-heptyl, n-octyl, n-nonyl, n-decyl, cyclopropyl, cyclopentyl or cyclohexyl; alkyl of from 1 to 20 carbon atoms, in particular of from 1 to 10 carbon atoms, having as substituents one or more halides, such as fluorine or chlorine, e.g. trifluoromethyl or 2,2,2-trifluoroethyl; $C_6$- to $C_{18}$-aryl, in particular $C_6$- to $C_{14}$-aryl, such as phenyl or naphthyl; substituted $C_6$- to $C_{18}$-aryl, in particular $C_6$- to $C_{14}$-aryl, having one or more substituents selected from the group consisting of alkyl which may be linear, branched or cyclic of from 1 to 10 carbon atoms, in particular of from 1 to 6 carbon atoms, such as methyl, ethyl, n-propyl, i-propyl, n-butyl, i-butyl, t-butyl or cyclohexyl, $C_6$- to $C_{10}$-aryl, such as phenyl, and halides, such as fluoride, chloride or bromide; CN; $C(=X^1)R^3$ as defined above, in particular $C(O)R^3$, $R^3$ being preferably selected from the group consisting of alkyl which may be linear, branched or cyclic having from 1 to 10 carbon atoms, such as methyl, ethyl, n-propyl, i-propyl, t-butyl or cyclohexyl, alkyl of from 1 to 10 carbon atoms having as substituents one or more halides, such as fluorine or chlorine, e.g. trifluoromethyl or 2,2,2-trifluoroethyl, aryl having from 6 to 14 carbon atoms, such as phenyl or naphthyl, and alkoxy having from 1 to 10 carbon atoms, such as O-methyl, O-ethyl, o-n-propyl, O-i-propyl, O-t-butyl or O-cyclohexyl; $C(=X^1)NR^4R^5$ as defined above, in particular $C(O)NR^4R^5$, $R^4$, $R^5$ being preferably selected from the group consisting of alkyl which may be linear, branched or cyclic having from 1 to 10 carbon atoms, such as methyl, ethyl, n-propyl, i-propyl or cyclohexyl, alkyl of from 1 to 10 carbon atoms having as substituents one or more halides, such as fluorine or chlorine, e.g. trifluoromethyl or 2,2,2-trifluoroethyl, aryl having from 6 to 14 carbon atoms, such as phenyl or naphthyl; and aralkyl having from 7 to 15 carbon atoms, such as benzyl; organosilyl having from 3 to 30 carbon atoms, in particular of from 3 to 18 carbon atoms, in which the tetravalent silicon atom is preferably substituted with radicals selected from the group consisting of alkyl which can be linear, branched or cyclic having from 1 to 20 carbon atoms, in particular of from 1 to 10 carbon atoms, such as methyl, ethyl, i-propyl, n-butyl, t-butyl or cyclohexyl, aryl having from 6 to 18 carbon atoms, in particular of from 6 to 10 carbon atoms, such as phenyl, and aralkyl, being formed from a $C_1$- to $C_6$-alkylene moiety, in particular a $C_1$- to $C_3$-alkylene moiety, and a $C_6$- to $C_{18}$-aryl moiety, in particular a $C_6$- to $C_{10}$-aryl moiety, such as benzyl, examples are trimethylsilyl, tri-i-propylsilyl, triphenylsilyl, t-butyldimethylsilyl or t-butyldiphenylsilyl; either $R^{10}$ or $R^{11}$ alone can be H, and $R^{10}$ and $R^{11}$ may be joined together to form a ring, having from 3 to 10 carbon atoms, such as cyclopropyl, cyclopentyl, cyclohexyl or said rings being unsaturated or having one or more annellated aromatic systems.

$R^{12}$ is H, alkyl of from 1 to 20 carbon atoms, in particular of from 1 to 10 carbon atoms, which may be linear, branched or cyclic such as methyl, ethyl, n-propyl, i-propyl or cyclohexyl, $C_6$- to $C_{18}$-aryl, in particular $C_6$- to $C_{10}$-aryl, such as phenyl or naphthyl, preferably phenyl, or a (co)polymer radical;

$R^{13}$ and $R^{14}$ are independently alkyl of from 1 to 20 carbon atoms, in particular of from 1 to 10 carbon atoms, which may be linear, branched or cyclic, such as methyl, ethyl, i-propyl or cyclohexyl, $C_6$- to $C_{18}$-aryl, in particular $C_6$- to $C_{10}$-aryl, such as phenyl or naphthyl, preferably phenyl, $C_7$- to $C_{20}$ aralkyl, in particular $C_7$- to $C_{15}$-aralkyl, such as benzyl, $C_3$- to $C_{30}$-organosilyl, in particular $C_3$- to $C_{18}$-organosilyl, in which the tetravalent silicon atom is preferably substituted with radicals selected from the group consisting of alkyl which can be linear, branched or cyclic having from 1 to 20 carbon atoms, in particular of from 1 to 10 carbon atoms, such as methyl, ethyl, i-propyl, n-butyl, t-butyl or cyclohexyl, aryl having from 6 to 18 carbon atoms, in particular of from 6 to 10 carbon atoms, such as phenyl, and aralkyl, being formed from a $C_1$- to $C_6$-alkylene moiety, in particular a $C_1$- to $C_3$-alkylene moiety, and a $C_6$- to $C_{18}$-aryl moiety, in particular a $C_6$- to $C_{10}$-aryl moiety, such as benzyl, examples are trimethylsilyl, triethylsilyl or triphenylsilyl; $C(=X^1)R^3$ as defined above, in particular $C(O)R^3$, $R^3$ being preferably selected from the group consisting of alkyl which may be linear, branched or cyclic having from 1 to 10 carbon atoms, such as methyl, ethyl, n-propyl, i-propyl, t-butyl or cyclohexyl; alkyl of from 1 to 10 carbon atoms having as substituents one or more halides, such as fluorine or chlorine, e.g. trifluoromethyl or 2,2,2-trifluoroethyl, aryl having from 6 to 14 carbon atoms, such as phenyl or naphthyl, and alkoxy having from 1 to 10 carbon atoms, such as O-methyl, O-ethyl, O-n-propyl, )-i-propyl, O-t-butyl or O-cyclohexyl; or $R^{13}$ and $R^{14}$ may be joined together to form a heterocycle, such as 2-pyrrolidone, 3,4-dihydropyrrol-2,5-dione or phthalimide.

$R^{15}$ and $R^{16}$ are independently alkyl which can be linear or branched of from 1 to 20 carbon atoms, in particular of from 1 to 10 carbon atoms, such as methyl, ethyl, n-propyl, i-propyl, t-butyl or cycloalkyl of from 3 to 10 carbon atoms, such as cyclohexyl; $C_6$- to $C_{18}$-aryl, in particular $C_6$- to $C_{14}$-aryl, such as phenyl or naphthyl;

$R^{17}$ is an organic radical of value p+q+r+s, in particular an alkylene of from 1 to 20 carbon atoms, preferably of from 2 to 10 carbon atoms, such as ethylene, 1,2-propylene, 1,3-propylene, 1,4-butylene or 1,6-hexylene, cycloalkylene of from 3 to 10 carbon atoms, such as 1,4-cyclohexylene, or $C_6$- to $C_{18}$-arylene, in particular $C_6$- to $C_{10}$-arylene, such as o-, m-, p-phenylene;

n is an integer of from 1 to 30.

In the context of the present invention, "heterocyclic rings capable of stabilizing an α-anion" refer to those heterocyclic rings which can stabilize a formal negative charge at a carbon atom covalently bound to the heterocyclic ring, such as is postulated for "living" anionic polymers. Thus, the vinyl group undergoing polymerization should be attached to the heterocyclic ring such that one or more of the heteroatoms in the heterocyclic ring stabilizes the negative charge on the "living" polymer intermediate. Accordingly, suitable vinyl heterocycles include 2-vinyl pyridine, 4-vinyl pyridine, 2-vinyl pyrrole, 5-vinyl pyrrole, 2-vinyl oxazole, 5-vinyl oxazole, 2-vinyl thiazole, 5-vinyl thiazole, 2-vinyl imidazole, 5-vinyl imidazole, 3-vinyl pyrazole, 5-vinyl pyrazole, 3-vinyl pyridazine, 6-vinyl pyridazine, 3-vinyl isoxazole, 3-vinyl isothiazoles, 2-vinyl pyrimidine, 4-vinyl pyrimidine, 6-vinyl pyrimidine, and any vinyl pyrazine, wherein 2-vinyl pyridine and 4-vinyl pyridine are preferred. The vinyl heterocycles mentioned above may bear one or more (preferably 1 or 2) $C_1$- to $C_6$-alkyl such as methyl, ethyl, n-propyl, i-propyl or cyclohexyl or $C_1$- to $C_6$-alkoxy groups such as methoxy, ethoxy, n-propoxy or i-propoxy, cyano groups, ester groups or halides such as chlorides. Further, those vinyl heterocycles which, when unsubstituted, contain an N—H group are protected at that position with a conventional blocking or protecting group, such as a $C_1$- to $C_6$-alkyl group, a $C_3$- to $C_{30}$-organo silyl group, an acyl group, etc.

If $R^{12}$ is a (co)polymer radical it may be derived from a homopolymer, a statistical copolymer or a block copolymer, irrespective of the method of making such (co)polymers. The (co)polymer radical $R^{12}$ can thus be obtained via anionic, radical or polycondensation methods. In this respect $R^{12}$ may represent for example a polymethylmethacrylate, a polystyrene, a polyether or a polyphenylene ether radical. The molecular weight $M_w$ of (co)polymer radical $R^{12}$ usually is in the range of 500 to 200 000 g/mol.

A preferred initiator component Q is $CR^{10}R^{11}R^{12}$. Preferably, $R^{10}$ and $R^{11}$ are independently phenyl or phenyl having from 1 to 3 substituents selected from the group consisting of alkyl of from 1 to 6 carbon atoms, such as methyl, ethyl, n-propyl, i-propyl, alkoxy of from 1 to 4 carbon atoms, such as methoxy, ethoxy, n-propoxy or i-propoxy, phenyl and halogen such as fluorine, chlorine or bromine; and $R^{12}$ is preferably H, alkyl of from 1 to 6 carbon atoms, phenyl, such as methyl, ethyl, n-propyl, i-propyl, or phenyl having from 1 to 3 substituents selected from the group consisting of alkyl of from 1 to 6 carbon atoms, such as methyl, ethyl, n-propyl, i-propyl, alkoxy of from 1 to 4 carbon atoms, such as methoxy, ethoxy, n-propoxy or i-propoxy, phenyl and halogen. Preferably, each of $R^{10}$, $R^{11}$ and $R^{12}$ is phenyl.

Examples of $R^{10}$ and $R^{11}$ being joined together to form a ring together with C include fluorenyl and indenyl ring systems as well as substituted derivatives thereof, such as benzindenyl.

Preferred initiator components Q are also ester enolates of esters formed from straight-chain or branched carboxylic acids and alcohols having from 1 to 6 carbon atoms, such as methyl isobutyrate or t-butylisobutyrate.

Another preferred initiator component Q is $[R^{17}(CR^{10}R^{11})_p(NR^{13})_q(O)_r(S)_s]^{n-}$ wherein p, q, r and s are independently an integer of from 0 to 30 and where the sum of p to s is at least 2. $R^{17}$ may be an organic radical of value n. $R^{17}$ is preferably an alkylene moiety of from 2 to 15 carbon atoms, cycloalkylene of from 3 to 10 carbon atoms or $C_6$- to $C_{14}$-arylene capable of bearing n functional groups, $(CR^{10}OR^{11})$, $(NR^{13})$, (O) and/or (S), as described above. Suitable as initiator components $Q^{2-}$ of type $R^{17}(CR^{10}R^{11})_2$ are for example 1,3-bis(1-methyl-alkan-1-yl)benzene, 1,3-bis(1-phenyl-alkan-1-yl)benzene or 1,1,4,4-tetraphenylbutan(1,4)diyl.

The present invention is also concerned with a method for preparing a compound corresponding to or containing

comprising the steps of:

reacting a phosphonium salt

with a metal salt selected from the group consisting of

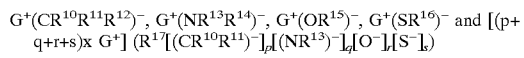

at a temperature of from more than 15° C., in the presence of an inert solvent, for a length of time sufficient to form a compound according to formula III, wherein $R^6$, $R^7$ and $R^8$ are independently $C_6$- to $C_{22}$-aryl, in particular $C_6$- to $C_{14}$-aryl, such as phenyl, naphthyl, fluorenyl, anthracenyl or phenanthryl, or substituted $C_6$- to $C_{22}$-aryl, in particular $C_6$- to $C_{14}$-aryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, n-butyl, i-butyl, t-butyl, n-pentyl, n-hexyl, n-heptyl, n-octyl, n-nonyl, n-decyl, n-undecyl, n-dodecyl, n-hexadecyl, cyclopropyl, cyclopentyl or cyclohexyl; oxyalkyl of from 1 to 20 carbon atoms, in particular of from 1 to 16 carbon atoms, in which alkyl may be linear, branched or cyclic, such as —O-methyl, —O-ethyl, —O-n-propyl, —O-i-propyl, —O-n-butyl, —O-i-butyl, —O-t-butyl, —O-n-pentyl, —O-n-hexyl, —O-n-heptyl, —O-n-octyl, —O-n-nonyl, —O-n-decyl, —O-n-dodecyl, —O-n-hexadecyl, —O-cyclopropyl, —O-cyclopentyl, —O-cyclohexyl, —O—$(CH_2CH_2O)_{1\ to\ 5}$—$CH_3$; $C_6$- to $C_{22}$-aryl, in particular $C_6$- to $C_{14}$-aryl, such as phenyl; substituted $C_6$- to $C_{22}$-aryl, in particular $C_6$- to $C_{14}$-aryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, t-butyl, n-dodecyl or cyclohexyl, oxy-$C_6$- to $C_{22}$-aryl, in particular oxy-$C_6$- to $C_{14}$-aryl, such as —O-phenyl; substituted oxy-$C_6$- to $C_{22}$-aryl, in particular oxy-$C_6$- to $C_{14}$-aryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, t-butyl, n-dodecyl or cyclohexyl; alkylene-oxy-alkyl of from 2 to 20 carbon atoms, in particular of from 3 to 17 carbon atoms, such as —$(CH_2)_{1\ to\ 5}$—O—$(CH_2CH_2O)_{0\ to\ 5}$—$CH_3$; aminodialkyl of from 2 to 30 carbon atoms, in particular of from 2 to 14 carbon atoms, such as dimethylamino, diethylamino, di(n-propyl)amino, di(i-propyl)amino, di(n-butyl)amino, di(i-butyl)amino, (methyl)(ethyl)amino; aminoalkylaryl of from 7 to 30 carbon atoms, in particular of from 7 to 15 carbon atoms, such as (methyl)(phenyl)amino, (ethyl)(phenyl)amino; aminodiaryl of from 12 to 36 carbon atoms, in particular of from 12 to 28 carbon atoms, such as diphenylamino, dinaphthylamino or (naphthyl)(phenyl)amino; halides, in particular fluoride, chloride, bromide or iodide, preferably fluoride, chloride or bromide; thio-alkyl of from 1 to 20 carbon atoms, in particular of from 1 to 16 carbon atoms, in which alkyl may be linear, branched or cyclic, such as —S-methyl, —S-ethyl, —S-n-propyl, —S-i-propyl, —S-n-butyl, —S-i-butyl, —S-t-butyl, —S-n-pentyl, —S-n-hexyl, —S-n-heptyl, —S-n-octyl, —S-n-nonyl, —S-n-decyl, —S-n-dodecyl, —S-n-hexadecyl, —S-cyclopropyl, —S-cyclopentyl, —S-cyclohexyl; thio-$C_6$- to $C_{22}$-aryl, in particular thio-$C_6$- to $C_{14}$-aryl, such as phenyl or naphthyl; substituted thio-$C_6$- to $C_{22}$-aryl, in particular thio-$C_6$- to $C_{14}$-aryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, n-butyl, i-butyl, t-butyl, n-dodecyl or cyclohexyl;

$R^9$ is $C_{10}$- to $C_{22}$-aryl, in particular $C_{10}$- to $C_{14}$-aryl, such as 1-naphthyl, 2-naphthyl, 1-anthracenyl, 2-anthracenyl, 9-anthracenyl, 1-phenanthryl, 2-phenanthryl, 3-phenanthryl, 4-phenanthryl or 9-phenanthryl, or substituted $C_{10}$- to $C_{22}$-aryl, in particular $C_{10}$- to $C_{14}$-aryl, such as 1-naphthyl, 2-naphthyl, 1-anthracenyl, 2-anthracenyl, 9-anthracenyl, 1-phenanthryl, 2-phenanthryl, 3-phenanthryl, 4-phenanthryl or 9-phenanthryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, n-butyl, i-butyl, t-butyl, n-pentyl, n-hexyl, n-heptyl, n-octyl, n-nonyl, n-decyl, n-undecyl, n-dodecyl, n-hexadecyl, cyclopropyl, cyclopentyl or cyclohexyl; oxyalkyl of from 1 to 20 carbon atoms, in particular of from 1 to 16 carbon atoms, in which the alkyl radical may be linear, branched or cyclic, such as —O-methyl, —O-ethyl, —O-n-propyl, —O-i-propyl, —O-n-butyl, —O-i-butyl, —O-t-butyl, —O-n-pentyl, —O-n-hexyl, —O-n-heptyl, —O-n-octyl, —O-n-nonyl, —O-n-decyl, —O-n-dodecyl, —O-n-hexadecyl, —O-cyclopropyl, —O-cyclopentyl, —O-cyclohexyl, —O—$(CH_2CH_2O)_{1\ to\ 5}$—$CH_3$; $C_6$- to $C_{22}$-aryl, in particular $C_6$- to $C_{14}$-aryl, such as phenyl; substituted $C_6$- to $C_{22}$-aryl, in particular $C_6$- to $C_{14}$-aryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, t-butyl, n-dodecyl or cyclohexyl; oxyaryl of from 6 to 22 carbon atoms, in particular of from 6 to 14 carbon atoms, such as —O-phenyl or —O-naphthyl; substituted oxy-aryl of from 6 to 22 carbon atoms, in particular of from 6 to 14 carbon atoms, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, n-butyl, i-butyl, t-butyl, n-dodecyl or cyclohexyl; alkylene-oxy-alkyl of from 2 to 20 carbon atoms, in particular of from 3 to 17 carbon atoms, such as —$(CH_2)_{1\ to\ 5}$—O—$(CH_2CH_2O)_{0\ to\ 5}$—$CH_3$; aminodialkyl of from 2 to 30 carbon atoms, in particular of from 2 to 14 carbon atoms, such as dimethylamino, diethylamino, di(n-propyl)amino, di(i-propyl)amino, di(n-butyl)amino, di(i-butyl)amino, (methyl)(ethyl)amino; amino(alkyl)(aryl) of from 7 to 30 carbon atoms, in particular of from 7 to 15 carbon atoms, such as (methyl)(phenyl)amino, (ethyl)(phenyl)amino; aminodiaryl of from 12 to 36 carbon atoms, in particular of from 12 to 28 carbon atoms, such as diphenylamino, dinaphthylamino or (naphthyl)(phenyl)amino; halides, in particular fluoride, chloride, bromide or iodide, preferably fluoride, chloride or bromide; thio-alkyl of from 1 to 20 carbon atoms, in particular of from 1 to 16 carbon atoms, in which alkyl may be linear, branched or cyclic, such as —S-methyl, —S-ethyl, —S-n-propyl, —S-i-propyl, —S-n-butyl, —S-i-butyl, —S-t-butyl, —S-n-pentyl, —S-n-hexyl, —S-n-heptyl, —S-n-octyl, —S-n-nonyl, —S-n-decyl, —S-n-dodecyl, —S-n-hexadecyl, —S-cyclopropyl, —S-cyclopentyl, —S-cyclohexyl; thio-$C_6$- to $C_{22}$-aryl, in particular thio-$C_6$- to $C_{14}$-aryl, such as thiophenyl; substituted thio-$C_6$- to $C_{22}$-aryl, in particular thio-$C_6$- to $C_{14}$-aryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, n-butyl, i-butyl, t-butyl, n-dodecyl or cyclohexyl, Q is $CR^{10}R^{11}R^{12}$, $NR^{13}R^{14}$, $OR^{15}$, $SR^{16}$ or $R^{17}(CR^{10}R^{11})_p(NR^{13})_q(O)_r(S)_s$ wherein p, q, r and s are independently an integer of from 0 to 30 and where the sum of p to s is at least 2;

$R^{10}$ and $R^{11}$ are independently alkyl which may be linear, branched or cyclic of from 1 to 20 carbon atoms, in particular of from 1 to 10 carbon atoms, such as methyl, ethyl, n-propyl, i-propyl, n-butyl, i-butyl, t-butyl, n-pentyl, n-hexyl, n-heptyl, n-octyl, n-nonyl, n-decyl, cyclopropyl, cyclopentyl or cyclohexyl; alkyl of from 1 to 20 carbon atoms, in particular of from 1 to 10 carbon atoms, having as substituents one or more halides, such as fluorine or chlorine, e.g. trifluoromethyl or 2,2,2-trifluoroethyl; $C_6$- to $C_{18}$-aryl, in particular $C_6$- to $C_{14}$-aryl, such as phenyl or naphthyl; substituted $C_6$- to $C_{18}$-aryl, in particular $C_6$- to $C_{14}$-aryl, having one or more substituents selected from the group consisting of alkyl which may be linear, branched or cyclic of from 1 to 10 carbon atoms, in particular of from 1 to 6 carbon atoms, such as methyl, ethyl, n-propyl, i-propyl, n-butyl, i-butyl, t-butyl or cyclohexyl, $C_6$- to $C_{10}$-aryl, such as phenyl, and halides, such as fluoride, chloride or bromide; CN; $C(=X^1)R^3$ as defined above, in particular $C(O)R^3$, $R^3$ being preferably selected from the group consisting of alkyl which may be linear, branched or cyclic having from 1 to 10 carbon atoms, such as methyl, ethyl, n-propyl, i-propyl, t-butyl or cyclohexyl, alkyl of from 1 to 10 carbon atoms having as substituents one or more halides, such as fluorine or chlorine, e.g. trifluoromethyl or 2,2,2-trifluoroethyl, aryl having from 6 to 14 carbon atoms, such as phenyl or naphthyl, and alkoxy having from 1 to 10 carbon atoms, such as O-methyl, O-ethyl, O-n-propyl, O-i-propyl, O-t-butyl or O-cyclohexyl; $C(=X^1)NR^4R^5$ as defined above, in particular $C(O)NR^4R^5$, $R^4$, $R^5$ being preferably selected from the group consisting of alkyl which may be linear, branched or cyclic having from 1 to 10 carbon atoms, such as methyl, ethyl, n-propyl, i-propyl or cyclohexyl, alkyl of from 1 to 10 carbon atoms having as substituents one or more halides, such as fluorine or chlorine, e.g. trifluoromethyl or 2,2,2-trifluoroethyl, aryl having from 6 to 14 carbon atoms, such as phenyl or naphthyl; and aralkyl having from 7 to 15 carbon atoms, such as benzyl; organosilyl having from 3 to 30 carbon atoms, in particular of from 3 to 18 carbon atoms, in which the tetravalent silicon atom is preferably substituted with radicals selected from the group consisting of alkyl which can be linear, branched or cyclic having from 1 to 20 carbon atoms, in particular of from 1 to 10 carbon atoms, such as methyl, ethyl, i-propyl, n-butyl, t-butyl or cyclohexyl, aryl having from 6 to 18 carbon atoms, in particular of from 6 to 10 carbon atoms, such as phenyl, and aralkyl, being formed from a $C_1$- to $C_6$-alkylene moiety, in particular a $C_1$- to $C_3$-alkylene moiety, and a $C_6$- to $C_{18}$-aryl moiety, in particular a $C_6$- to $C_{10}$-aryl moiety, such as benzyl, examples are trimethylsilyl, tri-i-propylsilyl, triphenylsilyl, t-butyldimethylsilyl or t-butyldiphenylsilyl; either $R^{10}$ or $R^{11}$ alone can be H, and $R^{10}$ and $R^{11}$ may be joined together to form a ring, having from 3 to 10 carbon atoms, such as cyclopropyl, cyclopentyl, cyclohexyl or said rings being unsaturated or having one or more annellated aromatic systems.

$R^{12}$ is H, alkyl of from 1 to 20 carbon atoms, in particular of from 1 to 10 carbon atoms, which may be linear, branched or cyclic such as methyl, ethyl, n-propyl, i-propyl or cyclohexyl, $C_6$- to $C_{18}$-aryl, in particular $C_6$- to $C_{10}$-aryl, such as phenyl or naphthyl, preferably phenyl, or a (co)polymer radical;

$R^{13}$ and $R^{14}$ are independently alkyl of from 1 to 20 carbon atoms, in particular of from 1 to 10 carbon atoms, which may be linear, branched or cyclic, such as methyl, ethyl, i-propyl or cyclohexyl, $C_6$- to $C_{18}$-aryl, in particular $C_6$- to $C_{10}$-aryl, such as phenyl or naphthyl, preferably phenyl, $C_7$- to $C_{20}$ aralkyl, in particular $C_7$- to $C_{15}$-aralkyl, such as benzyl, $C_3$- to $C_{30}$-organosilyl, in particular $C_3$- to $C_{18}$-organosilyl, in which the tetravalent silicon atom is preferably substituted with radicals selected from the group consisting of alkyl which can be linear, branched or cyclic having from 1 to 20 carbon atoms, in particular of from 1 to 10 carbon atoms, such as methyl, ethyl, i-propyl, n-butyl, t-butyl or cyclohexyl, aryl having from 6 to 18 carbon atoms, in particular of from 6 to 10 carbon atoms, such as phenyl, and aralkyl, being formed from a $C_1$- to $C_6$-alkylene moiety, in particular a $C_1$- to $C_3$-alkylene moiety, and a $C_6$- to $C_{18}$-aryl moiety, in particular a $C_6$- to $C_{10}$-aryl moiety, such as benzyl, examples are trimethylsilyl, triethylsilyl or triphenylsilyl; $C(=X^1)R^3$ as defined above, in particular $C(O)R^3$, $R^3$ being preferably selected from the group consisting of alkyl which may be linear, branched or cyclic having from 1 to 10 carbon atoms, such as methyl, ethyl, n-propyl, i-propyl, t-butyl or cyclohexyl; alkyl of from 1 to 10 carbon atoms having as substituents one or more halides, such as fluorine or chlorine, e.g. trifluoromethyl or 2,2,2-trifluoroethyl, aryl having from 6 to 14 carbon atoms, such as phenyl or naphthyl, and alkoxy having from 1 to 10 carbon atoms, such as O-methyl, O-ethyl, O-n-propyl, O-i-propyl, O-t-butyl or O-cyclohexyl; or $R^{13}$ and $R^{14}$ may be joined together to form a heterocycle, such as 2-pyrrolidone, 3,4-dihydropyrrol-2,5-dione or phthalimide.

$R^{15}$ and $R^{16}$ are independently alkyl which can be linear or branched of from 1 to 20 carbon atoms, in particular of from 1 to 10 carbon atoms, such as methyl, ethyl, n-propyl, i-propyl, t-butyl or cycloalkyl of from 3 to 10 carbon atoms, such as cyclohexyl; $C_6$- to $C_{18}$-aryl, in particular $C_6$- to $C_{14}$-aryl, such as phenyl or naphthyl;

$R^{17}$ is an organic radical of value p+q+r+s, in particular an alkylene of from 1 to 20 carbon atoms, preferably of from 2 to 10 carbon atoms, such as ethylene, 1,2-propylene, 1,3-propylene, 1,4-butylene or 1,6-hexylene, cycloalkylene of from 3 to 10 carbon atoms, such as 1,4-cyclohexylene, or $C_6$- to $C_{18}$-arylene, in particular $C_6$- to $C_{10}$-arylene, such as o-, m-, p-phenylene;

n is an integer of from 1 to 30.

$G^+$ is an inorganic cation and $T^-$ is an inorganic anion.

The $C_6$- to $C_{22}$-aryl in $R^9$ may be mono-, di-, poly- or persubstituted with substituents as defined above. Thus, naphthyl may be substituted or from 1 to 7 times, anthracenyl and phenanthryl of from 1 to 9 times. Preferably naphthyl, anthracenyl or phenanthryl may be substituted of from 1 to 5 times.

Thus, among other methods the initiators according to the present invention in which Q is $(CR^{10}R^{11}R^{12})$ can be conveniently prepared by cation exchange (metathesis) from the corresponding alkali or earth alkali metal carbanions and phosphonium salts, e.g. phosphonium halides. The metathesis reaction can be conducted at a temperature of from −78 to 120° C., preferably of from −30 to 80° C. and more preferably of from more than 15° C. Usually the initiators of the present invention are prepared by cation exchange at room temperature from the corresponding alkali or earth alkali metal carbanion and phosphonium halide salts. The alkali and earth alkali metal carbanion salts can be prepared in accordance with known procedures as for example described in Ch. Elschenbroich, A. Salzer, Organometallchemie, Teubner Verlag, Stuttgart, 1986 and references cited therein (e.g., treatment of a compound of the formula $R^{10}R^{11}R^{12}CH$ with an alkali metal hydride reagent; direct treatment of the compound of the formula $R^{10}R^{11}R^{12}CH$ with an alkali metal; by a metal-halide exchange between an alkali metal and the halide atom of a compound of the formula $R^{10}R^{11}R^{12}C(Ha1)$, where (Ha1) is chloride, bromide or iodide; or by carbometallation of alkenes or alkynes. Alkali metals include lithium, sodium, potassium, rubidium and cesium, preferably lithium and potassium, and most preferably potassium. Earth alkali metals include magnesium, calcium, strontium, barium, preferably magnesium.

The initiators according to the present invention in which Q is $NR^{13}R^{14}$, $OR^{15}$ or $SR^{16}$ can also be conveniently prepared by cation exchange at temperatures of from −78 to 120° C., preferably of from −30 to 80° C. and more preferably of from more than 15° C. from the corresponding alkali or earth alkali metal salts of nitrogen (amide), oxygen (alcoholate) or sulfur (thiolate) anions and phosphonium salts, e.g. phosphonium halides. The alkali and earth alkali metal amide, oxide (alcoholate) or sulfide (thiolate) salts can be prepared in accordance with known procedures (e.g. treatment of a compound of the formula $R^{10}R^{11}NH$, $R^{15}OH$ or $R^{16}SH$ with an alkali metal hydride reagent; direct treatment of the compound of the formula $R^{13}R^{14}NH$, $R^{15}OH$ or $R^{16}SH$ with an alkali metal; etc.). Alkali metals include lithium, sodium, potassium, rubidium and cesium, preferably lithium and potassium, and most preferably potassium. Earth alkali metals include magnesium, calcium, strontium, barium, preferably magnesium.

Polyanions of polyamines, polyols, polythiols or of compounds having a variety of the abovementioned functional groups, such as compounds according to the formula $R^{17}(CHR^{10}R^{11})_p(NHR^{13})_q(OH)_r(SH)_s$ are also suitable for the preparation of initiators in which Q is $R^{17}(CR^{10}R^{11})_p(NR^{13})_q(O)_r(S)_s$. These can also be prepared as described above by cation exchange at temperatures of from −78 to 120° C., preferably of from −30 to 80° C. and more preferably of from more than 15° C. from the corresponding alkali or earth alkali metal salts, e.g. by treatment of a compound $R^{17}(CHR^{10}R^{11}))_p(NHR^{13})_q(OH)_r(SH)_s$ with an alkali or earth alkali metal or with an alkali or earth alkali metal hydride reagent. Such initiators can be prepared from, for example, dianions like for example $[R^{17}(CR^{10}R^{11})_2]^{2-}$ wherein $R^{10}$ and $R^{11}$ are as defined above and $R^{17}$ is $-(CH_2CH_2)-$ by treating vinyl compounds with naphthyl sodium ($NaC_{10}H_8.^-$) (cf. M. Morton, Anionic Polymerization: Principles and Practice, Academic Press, New York, 1983), or from, for example, a diamide, a dialcoholate or a dithiolate, which is then metathesized with a tetrasubstituted phosphonium salt $[(R^6R^7R^8PR^9)^+][T^-]$, e.g. a phosphonium halide, to provide a multifunctional initiator of the formula $$[(R^6R^7R^8PR^9)^+]_n [R^{17}(CR^{10}R^{11})_p(NR^{13})_q(O)_r(S)_s]^{n-}$$

where $p+q+r+s \geq 2$, and wherein $R^6$, $R^7$, $R^8$, $R^9$, $R^{10}$, $R^{11}$, $R^{13}$ and $R^{17}$ are as defined above.

The alkali or earth alkali metal salts, e.g. halide salts, formed as a result of cation exchange can be filtered off prior to use of the initiator in polymerization, but filtration is not necessary for polymerization to be successful.

The cation metathesis reaction occurs very rapidly (e.g., within seconds) and quantitatively, even at −78° C., in concurrence with previous reports. A bathochromic shift in the maximum absorbance wavelength ($\lambda_{max}$) is observed during cation metathesis.

Many phosphonium reagents $(R^6R^7R^8PR^9)^+$ $T^-$, e.g. phosphonium halide, nitrate or borate salts, are commercially available. Others can be made by reacting a phosphine (i.e., a compound of the formula $PR^6R^7R^8$) with an alkyl or aryl halide of the formula $R^9(Hal)$ in accordance with known methods and procedures (cf. Horner et al., Chem. Ber. 1966, 99, 2782). Among others tris-triphenyl-2-naphthyl-phosphonium bromide or tris-triphenyl-1-naphthyl-phosphonium perchlorate can be prepared by these methods.

Also mixtures of initiators according to the present invention as disclosed above and below can be employed. Initiator mixtures can either be derived from species with differences in the phosphonium substituents or with differences in Q, or from differences in both. For example mixtures of carbanionic, amide, oxide or sulfide based initiators as well as mixtures of any combination of these species can be employed.

Initiators according to the present invention having as initiator compounds Q $^-CR^{10}R^{11}R^{12}$, $^-NR^{13}R^{14}$, or $^-OR^{15}$ or $^-SR^{16}$ can be employed in anionic polymerization methodology to form homo- or copolymers of, for example, acrylates or methacrylates.

The multifunctional initiators corresponding to or containing $[(R^6R^7R^8PR^9)^+]_n$ $[R^{17}(CR^{10}R^{11})_p(NR^{13})_q(O)_r(S)_s]^{n-}$ as mentioned above can be used in the process of the present invention to produce block copolymers such as branched, diblock, triblock or multi-block copolymers. Block copolymers can, for example, have a first, central poly(meth)acrylate or polyacrylonitrile block, and a second, distinct poly(meth)acrylate or polyacrylonitrile block at both ends of the first, central block.

Appropriate dianions as initiators for block copolymer synthesis according to the present invention are for example $$[(PR^6R^7R^8R^9)^+]_2 (R^{11}R^{12}C (R^{17})CR^{10}R^{11})^{2-}$$

$$[(PR^6R^7R^8R^9)^+]_2 (R^{10}N(R^{17})NR^{10})^{2-}$$

$$[(PR^6R^7R^8R^9)^+]_2 (OR^{17}O)^{2-}$$

$$[(PR^6R^7R^8R^9)^+]_2 (SR^{17}S)^{2-}$$

where $R^6$, $R^7$, $R^8$, $R^9$, $R^{10}$ and $R^{17}$ are as defined above. Such initiators can be used in the process of the present invention to make a triblock copolymer having, for example, a first, central poly(meth)acrylate or polyacrylonitrile block, and second, distinct poly(meth)acrylate or polyacrylonitrile blocks at the ends of the first, central block.

The present invention is thus also concerned with methods of making block copolymers of the formula $$A-(R^{11}R^{10}C (R^{17})CR^{10}R^{11})-A$$

$$A-(R^{13}N(R^{17})NR^{13})-A$$

$$A-(OR^{17}O)-A$$

$$A-(SR^{17}S)-A$$

$$B-A-(R^{11}R^{10}C(R^{17})CR^{10}R^{11})-A-B$$

$$B-A-(R^{13}N(R^{17})NR^{13})-A-B$$

$$B-A-(OR^{17}O)-A-B$$

$$B-A-(SR^{17}S)-A-B$$

$$C-B-A-(R^{11}R^{10}C(R^{17})CR^{10}R^{11})-A-B-C$$

$$C-B-A-(R^{13}N(R^{17})NR^{13})-A-B-C$$

$$C-B-A-(OR^{17}O)-A-B-C$$

$$C-B-A-(SR^{17}S)-A-B-C$$

etc. (i.e., with successive blocks attached to each end), where A, B and C are distinct (co)polymer blocks produced by anionic polymerization of one or more monomers of the formula:

(I)

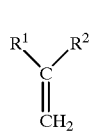

-continued

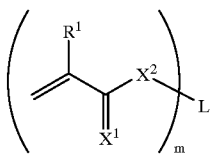
(II)

wherein $R^1$, $R^2$ $X^1$, $X^2$ and L are as defined above, using at least one of the present phosphonium salts of carbon, nitrogen-, oxygen- and sulfur-based anions.

Branched (co)polymers having three or more chains can be prepared from, for example, appropriate phosphonium salts of compounds having three or more carbonions, or nitrogen, oxygen and sulfur anions (so-called "multi-anionic" initiators), such as tris-, tetra-, penta- or hexa (hydroxymethyl)benzene, glycerol, erythritol, diethylene triamine, triethylene tetramine, dithioerythritol, dithiothreitol or trihydroxycyclohexane.

Generally initiator components of the formula $$[R^{17}(CR^{10}R^{11})_p(NR^{13}R^{14})_p(O)_r(S)_s]^{n-}$$

can be used for the production of branched or multiblock (co)polymers, where n can be at least 2, preferably from 2 to 6. Thus, a preferred initiator is one in which n is 2, and $R^{17}$ is —($CH_2CH_2$)—.

Triblock copolymers can be prepared from dianionic initiators described above by reacting the dianionic initiator with a first monomer to prepare a "living" anionic first block, followed by reacting the "living" anionic first block with a second monomer to provide terminal blocks on each end of the "living" first block. Thus, the present invention also concerns a method for preparing a triblock copolymer comprising:

mixing a first monomer of the formula I,

(I)

with an initiator of the formula $$[(PR^6R^7R^8R^9)^+]_2 \ [R^{17}(CR^{10}R^{11})_p(NR^{13})_q(O)_r(S)_s]^{2-}$$

and conducting the reaction at a temperature of from more than 40° C., in particular more than 45° C., in the presence or the absence of a solvent, for a length of time sufficient to polymerize the first monomer I, wherein the substituents and indices are as defined above, adding a second monomer of the formula I:

(I)

where $R^1$ and $R^2$ are as defined above, the second monomer being distinct from the first monomer, at a temperature of from more than 40° C., in particular more than 45° C. and reacting for a length of time sufficient to form a triblock (co)polymer intermediate, quenching the triblock (co)polymer intermediate with an acyl halide, an acid anhydride or a substance containing an active hydrogen atom to form a triblock (co) polymer; and isolating the formed triblock (co)polymer.

Successive blocks can be added to each end of the "living" anionic chain by successively adding different monomers or by changing reaction conditions appropriately (e.g., lowering the reaction temperature to increase or otherwise alter stereoregularity) after the first "adding" step above, but prior to quenching.

The present invention also encompasses an initiator corresponding to or containing a compound according to formula IV:

$$(R^6R^7R^8PR^9)^+ \ (Q')^- \qquad (IV),$$

wherein $R^6$, $R^7$ and $R^8$ are independently $C_6$- to $C_{22}$-aryl, in particular $C_6$- to $C_{14}$-aryl, such as phenyl, naphthyl, fluorenyl, anthracenyl or phenanthryl, or substituted $C_6$- to $C_{22}$-aryl, in particular $C_6$- to $C_{14}$-aryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, n-butyl, i-butyl, t-butyl, n-pentyl, n-hexyl, n-heptyl, n-octyl, n-nonyl, n-decyl, n-undecyl, n-dodecyl, n-hexadecyl, cyclopropyl, cyclopentyl or cyclohexyl; oxyalkyl of from 1 to 20 carbon atoms, in particular of from 1 to 16 carbon atoms, in which alkyl may be linear, branched or cyclic, such as —O-methyl, —O-ethyl, —O-n-propyl, —O-i-propyl, —O-n-butyl, —O-i-butyl, —O-t-butyl, —O-n-pentyl, —O-n-hexyl, —O-n-heptyl, —O-n-octyl, —O-n-nonyl, —O-n-decyl, —O-n-dodecyl, —O-n-hexadecyl, —O-cyclopropyl, —O-cyclopentyl, —O-cyclohexyl, —O—($CH_2CH_2O$)$_{1 \ to \ 5}$—$CH_3$; $C_6$- to $C_{22}$-aryl, in particular $C_6$- to $C_{14}$-aryl, such as phenyl; substituted $C_6$- to $C_{22}$-aryl, in particular $C_6$- to $C_{14}$-aryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, t-butyl, n-dodecyl or cyclohexyl, oxy-$C_6$- to $C_{22}$-aryl, in particular oxy-$C_6$- to $C_{14}$-aryl, such as —O-phenyl; substituted oxy-$C_6$- to $C_{22}$-aryl, in particular oxy-$C_6$- to $C_{14}$-aryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, t-butyl, n-dodecyl or cyclohexyl; alkylene-oxy-alkyl of from 2 to 20 carbon atoms, in particular of from 3 to 17 carbon atoms, such as —($CH_2$)$_{1 \ to \ 5}$—O—($CH_2CH_2O$)$_{0 \ to \ 5}$—$CH_3$; aminodialkyl of from 2 to 30 carbon atoms, in particular of from 2 to 14 carbon atoms, such as dimethylamino, diethylamino, di(n-propyl)amino, di(i-propyl)amino, di(n-butyl)amino, di(i-butyl)amino, (methyl)(ethyl) amino; aminoalkylaryl of from 7 to 30 carbon atoms, in particular of from 7 to 15 carbon atoms, such as (methyl)(phenyl)amino, (ethyl)(phenyl)amino; aminodiaryl of from 12 to 36 carbon atoms, in particular of from 12 to 28 carbon atoms, such as diphenylamino, dinaphthylamino or (naphthyl)(phenyl)amino; halides, in particular fluoride, chloride, bromide or iodide, preferably fluoride, chloride or bromide; thio-alkyl of from 1 to 20 carbon atoms, in particular of from 1 to 16 carbon atoms, in which alkyl may be linear, branched or cyclic, such as —S-methyl, —S-ethyl, —S-n-propyl, —S-i-propyl, —S-n-butyl, —S-i-butyl, —S-t-butyl, —S-n-pentyl, —S-n-hexyl, —S-n-heptyl, —S-n-octyl, —S-n-nonyl, —S-n-decyl, —S-n-dodecyl, —S-n-hexadecyl, —S-cyclopropyl, —S-cyclopentyl, —S-cyclohexyl; thio-$C_6$- to $C_{22}$-aryl, in particular thio-$C_6$- to $C_{14}$-aryl, such as phenyl or naphthyl; substituted thio-$C_6$- to $C_{22}$-aryl, in particular thio-$C_6$- to $C_{14}$-aryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, n-butyl, i-butyl, t-butyl, n-dodecyl or cyclohexyl;

$R^9$ is $C_{10}$- to $C_{22}$-aryl, in particular $C_{10}$- to $C_{14}$-aryl, such as 1-naphthyl, 2-naphthyl, 1-anthracenyl, 2-anthracenyl, 9-anthracenyl, 1-phenanthryl, 2-phenanthryl, 3-phenanthryl, 4-phenanthryl or 9-phenanthryl, or substituted $C_{10}$- to $C_{22}$-aryl, in particular $C_{10}$- to $C_{14}$-aryl, such as 1-naphthyl, 2-naphthyl, 1-anthracenyl, 2-anthracenyl, 9-anthracenyl, 1-phenanthryl, 2-phenanthryl, 3-phenanthryl, 4-phenanthryl or 9-phenanthryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, n-butyl, i-butyl, t-butyl, n-pentyl, n-hexyl, n-heptyl, n-octyl, n-nonyl, n-decyl, n-undecyl, n-dodecyl, n-hexadecyl, cyclopropyl, cyclopentyl or cyclohexyl; oxyalkyl of from 1 to 20 carbon atoms, in particular of from 1 to 16 carbon atoms, in which the alkyl radical may be linear, branched or cyclic, such as —O-methyl, —O-ethyl, —O-n-propyl, —O-i-propyl, —O-n-butyl, —O-i-butyl, —O-t-butyl, —O-n-pentyl, —O-n-hexyl, —O-n-heptyl, —O-n-octyl, —O-n-nonyl, —O-n-decyl, —O-n-dodecyl, —O-n-hexadecyl, —O-cyclopropyl, —O-cyclopentyl, —O-cyclohexyl, —O—$(CH_2CH_2O)_{1\ to\ 5}$—$CH_3$; $C_6$- to $C_{22}$-aryl, in particular $C_6$- to $C_{14}$-aryl, such as phenyl; substituted $C_6$- to $C_{22}$-aryl, in particular $C_6$- to $C_{14}$-aryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, t-butyl, n-dodecyl or cyclohexyl; oxyaryl of from 6 to 22 carbon atoms, in particular of from 6 to 14 carbon atoms, such as —O-phenyl or —O-naphthyl; substituted oxy-aryl of from 6 to 22 carbon atoms, in particular of from 6 to 14 carbon atoms, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, n-butyl, i-butyl, t-butyl, n-dodecyl or cyclohexyl; alkylene-oxy-alkyl of from 2 to 20 carbon atoms, in particular of from 3 to 17 carbon atoms, such as —$(CH_2)_{1\ to\ 5}$—O—$(CH_2CH_2O)_{0\ to\ 5}$—$CH_3$; aminodialkyl of from 2 to 30 carbon atoms, in particular of from 2 to 14 carbon atoms, such as dimethylamino, diethylamino, di(n-propyl)amino, di(i-propyl)amino, di(n-butyl)amino, di(i-butyl)amino, (methyl)(ethyl)amino; aminoalkylaryl of from 7 to 30 carbon atoms, in particular of from 7 to 15 carbon atoms, such as (methyl)(phenyl)amino, (ethyl)(phenyl)amino; aminodiaryl of from 12 to 36 carbon atoms, in particular of from 12 to 28 carbon atoms, such as diphenylamino, dinaphthylamino or (naphthyl)(phenyl)amino; halides, in particular fluoride, chloride, bromide or iodide, preferably fluoride, chloride or bromide; thio-alkyl of from 1 to 20 carbon atoms, in particular of from 1 to 16 carbon atoms, in which alkyl may be linear, branched or cyclic, such as —S-methyl, —S-ethyl, —S-n-propyl, —S-i-propyl, —S-n-butyl, —S-i-butyl, —S-t-butyl, —S-n-pentyl, —S-n-hexyl, —S-n-heptyl, —S-n-octyl, —S-n-nonyl, —S-n-decyl, —S-n-dodecyl, —S-n-hexadecyl, —S-cyclopropyl, —S-cyclopentyl, —S-cyclohexyl; thio-$C_6$- to $C_{22}$-aryl, in particular thio-$C_6$- to $C_{14}$-aryl, such as thiophenyl; substituted thio-$C_6$- to $C_{22}$-aryl, in particular thio-$C_6$- to $C_{14}$-aryl, having one or more substituents selected from the group consisting of alkyl which may be linear, branched or cyclic of from 1 to 20 carbon atoms, in particular of from 1 to 16 carbon atoms, such as methyl, ethyl, n-propyl, i-propyl, n-butyl, i-butyl, t-butyl, n-dodecyl or cyclohexyl;

Q' is $R^{18}$—$CR^{10}R^{11}R^{12}$, $R^{18}$—$NR^{13}R^{14}$, $R^{18}$—$OR^{15}$, $R^{18}$—$SR^{16}$, $R^{18}$—Z;

$R^{10}$ and $R^{11}$ are independently alkyl which may be linear, branched or cyclic of from 1 to 20 carbon atoms, in particular of from 1 to 10 carbon atoms, such as methyl, ethyl, n-propyl, i-propyl, n-butyl, i-butyl, t-butyl, n-pentyl, n-hexyl, n-heptyl, n-octyl, n-nonyl, n-decyl, cyclopropyl, cyclopentyl or cyclohexyl; alkyl of from 1 to 20 carbon atoms, in particular of from 1 to 10 carbon atoms, having as substituents one or more halides, such as fluorine or chlorine, e.g. trifluoromethyl or 2,2,2-trifluoroethyl; $C_6$- to $C_{18}$-aryl, in particular $C_6$- to $C_{14}$-aryl, such as phenyl or naphthyl; substituted $C_6$- to $C_{18}$-aryl, in particular $C_6$- to $C_{14}$-aryl, having one or more substituents selected from the group consisting of alkyl which may be linear, branched or cyclic of from 1 to 10 carbon atoms, in particular of from 1 to 6 carbon atoms, such as methyl, ethyl, n-propyl, i-propyl, n-butyl, i-butyl, t-butyl or cyclohexyl, $C_6$- to $C_{10}$-aryl, such as phenyl, and halides, such as fluoride, chloride or bromide; CN; $C(=X^1)R^3$ as defined above, in particular $C(O)R^3$, $R^3$ being preferably selected from the group consisting of alkyl which may be linear, branched or cyclic having from 1 to 10 carbon atoms, such as methyl, ethyl, n-propyl, i-propyl, t-butyl or cyclohexyl, alkyl of from 1 to 10 carbon atoms having as substituents one or more halides, such as fluorine or chlorine, e.g. trifluoromethyl or 2,2,2-trifluoroethyl, aryl having from 6 to 14 carbon atoms, such as phenyl or naphthyl, and alkoxy having from 1 to 10 carbon atoms, such as O-methyl, O-ethyl, O-n-propyl, O-i-propyl, O-t-butyl or O-cyclohexyl; $C(=X^1)NR^4R^5$ as defined above, in particular $C(O)NR^4R^5$, $R^4$, $R^5$ being preferably selected from the group consisting of alkyl which may be linear, branched or cyclic having from 1 to 10 carbon atoms, such as methyl, ethyl, n-propyl, i-propyl or cyclohexyl, alkyl of from 1 to 10 carbon atoms having as substituents one or more halides, such as fluorine or chlorine, e.g. trifluoromethyl or 2,2,2-trifluoroethyl, aryl having from 6 to 14 carbon atoms, such as phenyl or naphthyl and aralkyl having from 7 to 15 carbon atoms, such as benzyl; organosilyl having from 3 to 30 carbon atoms, in particular of from 3 to 18 carbon atoms, in which the tetravalent silicon atom is preferably substituted with radicals selected from the group consisting of alkyl which can be linear, branched or cyclic having from 1 to 20 carbon atoms, in particular of from 1 to 10 carbon atoms, such as methyl, ethyl, i-propyl, n-butyl, t-butyl or cyclohexyl, aryl having from 6 to 18 carbon atoms, in particular of from 6 to 10 carbon atoms, such as phenyl, and aralkyl, being formed from a C1- to $C_6$-alkylene moiety, in particular a $C_1$- to $C_3$-alkylene moiety, and a $C_6$- to $C_{18}$-aryl moiety, in particular a $C_6$- to $C_{10}$-aryl moiety, such as benzyl, examples are trimethylsilyl, tri-i-propylsilyl, triphenylsilyl, t-butyldimethylsilyl or t-butyldiphenylsilyl; either $R^{10}$ or $R^{11}$ alone can be H, or $R^{10}$ and $R^{11}$ may be joined together to form a ring having from 3 to 10 carbon atoms, such as cyclopropyl, cyclopentyl, cyclohexyl, and or said rings being unsaturated or having one or more annellated aromatic systems.

$R^{12}$ is H, alkyl of from 1 to 20 carbon atoms, in particular of from 1 to 10 carbon atoms, which may be linear, branched or cyclic such as methyl, ethyl, n-propyl, i-propyl or cyclohexyl, $C_6$- to $C_{18}$-aryl, in particular $C_6$- to $C_{10}$-aryl, such as phenyl or naphthyl, preferably phenyl, or a (co)polymer radical;

$R^{13}$ and $R^{14}$ are independently alkyl of from 1 to 20 carbon atoms, in particular of from 1 to 10 carbon atoms, which may be linear, branched or cyclic, such as methyl, ethyl, i-propyl or cyclohexyl; $C_6$- to $C_{18}$-aryl, in particular $C_6$- to $C_{10}$-aryl, such as phenyl or naphthyl, preferably phenyl; $C_7$- to $C_{20}$ aralkyl, in particular $C_7$- to $C_{15}$-aralkyl, such as benzyl; $C_3$- to $C_{30}$-organosilyl, in particular $C_3$- to $C_{18}$-organosilyl, in which the tetravalent silicon atom is preferably substituted with radicals selected from the group consisting of alkyl which can be linear, branched or cyclic having from 1 to 20 carbon atoms, in particular of from 1 to 10 carbon atoms, such as methyl, ethyl, i-propyl, n-butyl, t-butyl or cyclohexyl, aryl having from 6 to 18 carbon atoms, in particular of from 6 to 10 carbon atoms, such as phenyl, and aralkyl, being formed from a $C_1$- to $C_6$-alkylene moiety, in particular a $C_1$- to $C_3$-alkylene moiety, and a $C_6$- to $C_{18}$-aryl moiety, in particular a $C_6$- to $C_{10}$-aryl moiety, such as benzyl, examples are trimethylsilyl, triethylsilyl or triphenylsilyl; $C(=X^1)R^3$ as defined above, in particular $C(O)R^3$, $R^3$ being preferably selected from the group consisting of alkyl which may be linear, branched or cyclic having from 1 to 10 carbon atoms, such as methyl, ethyl, n-propyl, i-propyl, t-butyl or cyclohexyl, alkyl of from 1 to 10 carbon atoms having as substituents one or more halides, such as fluorine or chlorine, e.g. trifluoromethyl or 2,2,2-trifluoroethyl, aryl having from 6 to 14 carbon atoms, such as phenyl or naphthyl, and alkoxy having from 1 to 10 carbon atoms, such as O-methyl, O-ethyl, O-n-propyl, )-i-propyl, O-t-butyl or O-cyclohexyl; or $R^{13}$ and $R^{14}$ may be joined together to form a heterocycle, such as 2-pyrrolidone, 3,4-dihydropyrrol-2,5-dione or phthalimide;

$R^{15}$ and $R^{16}$ are independently alkyl which can be linear or branched of from 1 to 20 carbon atoms, in particular of from 1 to 10 carbon atoms, such as methyl, ethyl, n-propyl, i-propyl, t-butyl or cycloalkyl of from 3 to 10 carbon atoms, such as cyclohexyl; $C_6$- to $C_{18}$-aryl, in particular $C_6$- to $C_{14}$-aryl, such as phenyl or naphthyl;

$R^{18}$ is a (co)polymer radical;

Z is a radical derived from an initiator for the anionic polymerization of anionic polymerizable monomers other than radicals derived from compounds III or IV. The $C_6$- to $C_{22}$-aryl in $R^9$ may be mono-, di-, poly- or persubstituted with substituents as defined above. Thus, naphthyl may be substituted or from 1 to 7 times, anthracenyl and phenanthryl of from 1 to 9 times. Preferably naphthyl, anthracenyl or phenanthryl may be substituted of from 1 to 5 times.

The (co)polymer group $R^{18}$ can for example be derived from an anionic polymerization of one or more anionically polymerizable monomers by which a living polymer species is obtained or by a polymerization process according to the present invention.

Thus, the present invention is also concerned with a method for preparing an initiator corresponding to or containing $(R^6R^7R^8PR^9)^+$ $(Q')^-$ (IV), comprising the steps of mixing a monomer of the formula I or of the monomer II or a mixture of monomers of formula I and II with an initiator corresponding to or containing $(R^6R^7R^8PR^9)^+$ $(Q)^-$ (III), wherein $R^6$ to $R^9$ are as defined above and Q is $CR^{10}R^{11}R^{12}$, $NR^{13}R^{14}$, $OR^{15}$ or $SR^{16}$ wherein $R^{10}$ to $R^{16}$ are as defined above, and conducting the reaction at a temperature of from more than 40° C., in the presence or the absence of a solvent, for a length of time sufficient to polymerize the monomer(s) and to form a reaction mixture, and thus to form compound IV, in which $R^{18}$ represents the living polymer chain according to the invention; and isolating the formed compound IV without a quenching step, wherein $R^1$, $R^2$, $X^1$, $X^2$, $R^3$, $R^4$, $R^5$ and $R^{18}$ are as defined above.

Such an initiator can also be obtained by anionically polymerizing one or more anionically polymerizable monomers and to form a living (co)polymer anion salt $$G^+(R^{18}-Z)^-,$$

where $G^+$ is an inorganic cation, in particular a cation selected from the group consisting of elements of group IA, IIA and IIIA of the periodic table of the elements, such as lithium, sodium, potassium, magnesium, calcium, bor or aluminum. $R^{18}$ is a (co)polymer radical, having for instance molecular weight of from 500 to 300 000 g/mol, in particular of from 1 000 to 100 000 g/mol. Z may be a radical derived from an initiator for the anionic polymerization of anionic polymerizable monomers other than radicals derived from compounds III or IV. Radicals Z may either stem from alkali organyl or earth alkali organyl compounds, e.g. n-butyl lithium or s-butyl lithium, or from metal-free systems like the ester enolate/protonated P4-phosphazene base system by Seebach and Pietzonka (vide infra) or the alkoxide/n-$Bu_4N^+$ system by Reetz et al (vide infra). Thus Z may be for example a butyl, a C—C-linked ester or an O-linked alkoxy moiety.

Said (co)polymer anion salt is metathesized with a phosphonium salt of the formula $(R^6R^7R^8PR^9)^+$ $T^-$, wherein $T^-$ is an inorganic anion, and $R^6$, $R^7$, $R^8$ and $R^9$ are as defined above, at a temperature in the range of −78 to 120° C. to provide compound IV. $T^-$ is preferably selected from the group consisting of a halide, nitrate, nitrite, borate, tetraphenyl borate $[Ph_4B^-]$, tosylate $[p-H_3CC_6H_4SO_3^-]$, one-half equivalent of sulfite [or "$SO_3)_{0.5}$"], trifluoromethanesulfonate, on-half equivalent of sulfate [or "$(SO_4)_{0.5}$"].

Living (co)polymer anion salts can be prepared in accordance with known methods, for example, by an organometal reagent initiated (e.g., a $C_1$–$C_4$-alkyllithium-initiated) polymerization of an anionically polymerizable monomer (e.g. styrene). These compounds can be used to initiate the polymerization of the next comonomer. Suitable monomers for preparation of such a "living" (co)polymeric anion include styrene, α-methylstyrene, styrene or α-methylstyrene having 1 to 5 (preferably 1 to 3, most preferably 1) $C_1$–$C_4$-alkyl and/or $C_1$–$C_4$-alkoxy substituents on the phenyl ring, butadiene, isoprene, dimethylbutadiene, or mixtures thereof. Preferably the (co)polymer anion is endcapped. Thus, the (co)polymeric anion salt can, for example, be reacted with a 1,1-diarylethylene (for example, 1,1-diphenylethylene) to form a (co)polymer diarylmethyl anion, which is then metathesized with a tetrasubstituted phosphonium halide to provide an initiator of the formula:

(co)polymer-(CH$_2$CAr$_2$)$^-$ (PR$^6$R$^7$R$^8$R$^9$)$^+$ where Ar is an aryl group as defined above.

Living (co)polymer anions as described above can also be reacted with, for example, aziridine, an epoxide or a thiirane to form (co)polymer initiators of the following formulas:

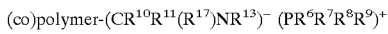
(co)polymer-(CR$^{10}$R$^{11}$(R$^{17}$)NR$^{13}$)$^-$ (PR$^6$R$^7$R$^8$R$^9$)$^+$

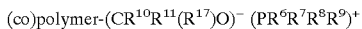
(co)polymer-(CR$^{10}$R$^{11}$(R$^{17}$)O)$^-$ (PR$^6$R$^7$R$^8$R$^9$)$^+$

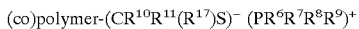
(co)polymer-(CR$^{10}$R$^{11}$(R$^{17}$)S)$^-$ (PR$^6$R$^7$R$^8$R$^9$)$^+$ where R$^{10}$, R$^{11}$, R$^{13}$ and R$^{17}$ are as defined above.

Initiators according to formula IV which are obtained according to the method of the present invention may also be directly employed, i.e. without an isolating step, in the polymerization of monomers of the formula I or II which are distinct from the first monomers used. Monomer(s) of the formula I or II can then either be added to the initiator IV, neat or in solution, at a temperature of above or below 40° C.

The isolating step for compound IV is conducted in accordance with known procedures and methods, such as precipitating the polymeric initiator and filtering the precipitated initiator. Precipitation can be conducted using a suitable inert non-solvent, such as a C$_5$–C$_8$-alkane or -cycloalkane, e.g. hexan, heptane, cyclohexane, pentane or mineral spirits. Preferably, the non-solvent for precipitating is hexane or mixtures of hexanes.

The (co)polymeric initiators corresponding to or containing a compound according to formula IV are then used to initiate the polymerization of the next anionically polymerizable comonomer (preferably of the formulas (I) or (II) as described above). These initiators can for instance be used in the process of the present invention to make a block copolymer having, for example, a first polystyrene block and a second poly(meth)acrylate or polyacrylonitrile block.

Thus, the present invention also encompasses a method for preparing a block (co)polymer, comprising the steps of:

mixing a monomer of the formula I, or a monomer of the formula II, or a mixture of both I and II:

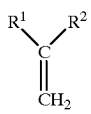
(I)

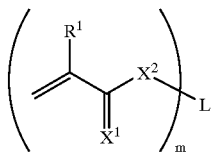
(II)

with an initiator corresponding to or containing

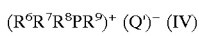
(R$^6$R$^7$R$^8$PR$^9$)$^+$ (Q')$^-$ (IV)

and conducting the reaction at a temperature of from more than 40° C., in the presence or absence of a solvent, for a length of time sufficient to polymerize the monomer(s) and form a reaction mixture, and quenching the reaction mixture with an acyl halide, an acid anhydride or a substance containing an active hydrogen atom to form a (co)polymer; and isolating the formed (co)polymer, wherein the substituents R$^1$ to R$^{16}$, R$^{18}$, X$^1$, X$^2$, L, Q, and Z as well as the index m are as defined above.

The present invention is thus also concerned with a method of making block copolymers of the formula:

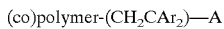
(co)polymer-(CH$_2$CAr$_2$)—A

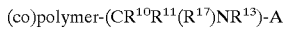
(co)polymer-(CR$^{10}$R$^{11}$(R$^{17}$)NR$^{13}$)-A

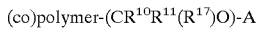
(co)polymer-(CR$^{10}$R$^{11}$(R$^{17}$)O)-A

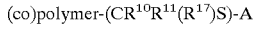
(co)polymer-(CR$^{10}$R$^{11}$(R$^{17}$)S)-A where (co)polymer is one produced by anionic polymerization (preferably of styrene, α-methylstyrene, styrene or α-methylstyrene having 1 to 5 C$_1$–C$_4$-alkyl and/or C$_1$–C$_4$-alkoxy substituents on the phenyl ring, butadiene, isoprene, dimethylbutadiene, or mixtures thereof), R$^{10}$, R$^{11}$, R$^{13}$, R$^{17}$ and Ar are as defined above, and A is one or more distinct (co)polymer blocks of one or more monomers of the formula:

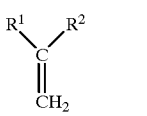
(I)

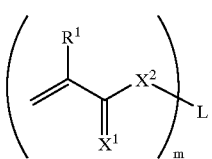
(II)

where R$^1$, R$^2$, X$^1$, X$^2$, L and m are as defined above and (co)polymer refers to Q' as defined above.

Generally the method of making block copolymers also encompasses the synthesis of compounds like, for example, (co)polymer-A, where (co)polymer is one produced by anionic polymerization as described above, in particular a homo- or copolymer of acrylates or methacrylates, and A is one or more distinct (co)polymer blocks of one or more monomers of formula I or II.

The weight or number average molecular weight of a block in the present block (co)polymers may range from 300 to 500,000 g/mol, more preferably 500 to 300,00 g/mol, and most preferably from 1,000 to 100,000 g/mol. Similar to the monodisperse (co)polymer described above, the weight or number average molecular weight of block B in the present triblock copolymer may range from 500 g/mol to 300,000 g/mol, preferably from 1,000 to 200,000 g/mol, and more preferably from 2,000 to 60,000 g/mol. The present block copolymers are also preferably narrow in molecular weight in that they may have a M$_w$/M$_n$ value of <2.0, preferably <1.5, and most preferably <1.2. Successive blocks may also be of the same monomer, but have a different tacticity.

The polymerization methods described can be conducted with or without a solvent. In the context of the present invention when a small quantity of liquid is required to solubilize or partially solubilize the initiator the polymerization is still run without a solvent.

Suitable solvents for the reacting or polymerizing step of the present method (in any of its various embodiments)

include ethers, cyclic ethers, aliphatic and aromatic hydrocarbon solvents, and mixtures thereof. Suitable ethers include compounds of the formula $R^{19}OR^{20}$, in which each of $R^{19}$ and $R^{20}$ is independently an alkyl group of from 1 to 6 carbon atoms which may be further substituted with a $C_1$–$C_4$-alkoxy group.

Preferably, when one of $R^{19}$ and $R^{20}$ is methyl, the other of $R^{19}$ and $R^{20}$ is alkyl of from 4 to 6 carbon atoms or $C_1$–$C_4$-alkoxyethyl. Examples include diethyl ether, ethyl propyl ether, dipropyl ether, methyl t-butyl ether, di-t-butyl ether, glyme (dimethoxyethane), diglyme (diethylene glycol dimethyl ether), etc.

Suitable cyclic ethers include THF and dioxane. Suitable aromatic hydrocarbon solvents include benzene, toluene, o-xylene, m-xylene, p-xylene and any isomer or mixture of isomers of cumene. Suitable aliphatic hydrocarbon solvents include linear and cyclic compounds, such as hexane, cyclohexane or mineral spirits.

The initiator should be at least partially soluble in the solvent. Thus, when using an aromatic solvent, the reaction may be advantageously promoted by increasing the lipophilicity of the initiator (e.g., having a $C_6$–$C_{20}$-alkyl substituent in one or both of the ionic components [preferably at least in the phosphonium cation]). For example, if the initiator has the formula $(R^6R^7R^8PR^9)^+$ $(CR^{10}R^{11}R^{12})^-$ or $(R^6R^7R^8PR^9)^+$ $(NR^{13}R^{14})^-$, where $R^6$ to $R^{14}$ are independently an aryl group, one or more of these aryl groups should include one or more alkyl substituents having from 1 to 20 carbon atoms, preferably having from 4 to 20 carbon atoms and more preferably having form 6 to 20 carbon atoms. To avoid molecular weight distribution broadening, the polymer should also be soluble in the solvent selected.

The polymerization may be conducted by addition of a solution of monomer into a solution of initiator. The monomer may also be added as such, i.e. without any solvent, to a solution of the initiator. It is also within the context of the present invention to add the initiator to the monomer(s) or to the monomer solution, respectively. The initiator may be added neat, partially dissolved or completely dissolved.

The polymerization reaction can also be conducted in the absence of a solvent. According to the invention absence of a solvent does not exclude the addition of an initiator which is dissolved or partially dissolved in an inert solvent, which does not quench the reaction, to the reaction mixture.

According to the present invention the monomer(s) and the initiator are mixed at a temperature of at or below 40° C. However, mixing may also take place at temperatures of above 40° C. For reasons of convenience mixing of monomer(s) and initiator is usually conducted at room temperature. The reaction mixture can then immediately be heated to a temperature of above 40° C. or can be kept below 40° C. for several minutes to hours prior to heating to a temperature of above 40° C. Polymerizations according to the present invention can also be conducted under adiabatic or nearly adiabatic conditions.

When the polymerization reaction is very exothermic a preferred temperature can be achieved by cooling the reaction in a controlled manner.

Although the present invention may be conducted at a temperature of from 40° C. to 150° C., the preferred range is from 45° C. to 140° C., more preferably from 50° C. to 130° C., even more preferably from 60° C. to 130° C., and most preferably from 65° C. to 120° C.

It is believed that there exists an equilibrium between a dormant than 95% of all species) and a polymerization active species (phosphonium enolate, probably present in an amount of less than 5% of all species) such as is indicated in the scheme below:

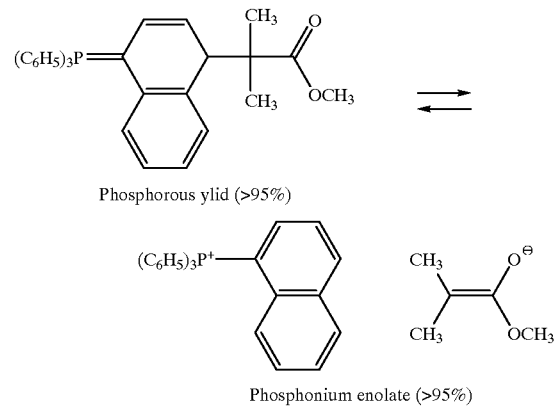

Phosphorous ylid (>95%)

Phosphonium enolate (>95%)

Thus, the initiators according to the invention as described above correspond to or contain for example compounds according to formula (III): $[(R^6R^7R^8PR^9)^+]_n Q^{n-}$ or formula (IV):

$[(R^6R^7R^8PR^9)^+] (Q')^-$.

The present isolating step is conducted in accordance with known procedures and methods, such as quenching the reaction mixture, precipitating the (co)polymer and filtering off the precipitated (co)polymer. Precipitation can be conducted using a suitable $C_5$–$C_8$-alkane or cycloalkane non-solvent, such as hexane, heptane, cyclohexane, pentane, mineral spirits, or a $C_1$–$C_6$-alcohol, such as methanol, ethanol or isopropanol, or any mixture of suitable non-solvents. Preferably, the non-solvent for precipitating is hexane, mixtures of hexanes, or methanol.

Suitable quenching reagents for the termination of the polymerization in the present process include acyl halides, acid anhydrides and substances containing an active hydrogen atom.

Suitable acyl halides include halides, preferably chlorides, of organic acids, including carboxylic acids, sulfonic acids, phosphonic acids, etc. Such acids are suitably of the formula $R^{21}CO$ (Hal), $R^{21}SO_2$ (Hal) and $R^{21}P(=O)(OR^{22})$ (Hal), in which $R^{21}$ is alkyl of from 1 to 20 carbon atoms in which each of the hydrogen atoms may be independently replaced by a halide (preferably a fluoride or a chloride), alkenyl of from 2 to 20 carbon atoms, alkynyl of from 1 to 10 carbon atoms, phenyl which may be substituted with from 1 to 5 halogen atoms or alkyl groups of from 1 to 4 carbon atoms, or aralkyl in which the aryl group is phenyl of substituted phenyl and the alkyl group is from 1 to 6 carbon atoms; (Hal) is a fluorine, chlorine, bromine or iodine atom; and $R^{22}$ is alkyl of from 1 to 4 carbon atoms. Preferred acyl halides include benzenesulfonyl chloride, toluenesulfonyl chloride and those of the formula $R^{23}CO$ (Hal), in which $R^{23}$ is alkyl of from 1 to 4 carbon atoms, such as methyl, ethyl, n-propyl or i-propyl, vinyl, 2-propenyl or phenyl, and (Hal) is chlorine (e.g., acetyl chloride, propionyl chloride, (meth)acryloyl chloride and benzoyl chloride). The most preferred acyl halide is methacryloyl chloride.

Suitable acid anhydrides include those of the formula $(R^{23}CO)_2O$, where $R^{23}$ is as defined above. Preferred acid anhydrides include acetic anhydride, propionic anhydride, and (meth)acrylic anhydride.

Active hydrogen atom-containing substances include those substances in which a hydrogen atom is attached to a heteroatom, and which have a $pK_a$ less than the protonated nitrogen, oxygen or sulfur anion of the initiator. Such compounds include water, alcohols of from 1 to 6 carbon atoms, aqueous solutions of ammonium salts (e.g., ammonium halide or ammonium carbonates), carboxylic and mineral acids (e.g., acetic acid, hydrochloric acid, etc.) or an aqueous solution thereof, etc., with acetic acid being the most preferred quenching agent.

However, if it is desired to isolate the living polymer by omitting the quenching step, only inert and anhydrous aprotic solvents, such as $C_5$–$C_8$-alkane or cycloalkane solvents, can be used for precipitation and washing. The precipitated (co)polymer can be filtered off by gravity or by vacuum filtration, in accordance with known methods (e.g., using a Büchner funnel and an aspirator). The polymer can then be washed with the liquid used to precipitate the polymer, if desired. The steps of precipitating, filtering and washing may be repeated, as desired. Care has to be taken in the isolation of the living polymer in that moisture should be excluded from the precipitation, washing and drying steps.

Once isolated, the (co)polymer may be dried by drawing air or an inert gas, e.g. nitrogen, through the (co)monomer, by vacuum, etc., in accordance with known methods (preferably by vacuum). The present (co)polymer may be analyzed and/or characterized by size exclusion chromatography, in accordance with known procedures.

The syndiotactic content of PMMA prepared by the present process at 70° C. is moderately high.

The reaction can be carried out in any suitable reactor, e.g. in a batch system or in a continuous flow system. Homo-and statistical copolymers can be prepared in a continuous stirring tank reactor.

The polymers produced by the present method have a narrow molecular weight distribution. The ratio of weight average molecular weight to number average molecular weight ($M_w/M_n$) is usually below 2.0, more preferably of 1.5 or less, and most preferably of 1.2 or less.

The number average molecular weight of polymer produced by the present method depends linearly on the conversion.

Having generally described this invention, a further understanding can be obtained by reference to certain specific examples which are provided herein for purposes of illustration only and are not intended to be limiting unless otherwise specified.

EXAMPLE

Reagents and solvents

The work was carried out under nitrogen. Tetrahydrofurane (THF) as titrated with tritylpotassium/THF solution to a persistent red color and then recondensed under reduced pressure.

Triphenylmethane was dried for 8 h under reduced pressure and then admixed in THF with Na—K alloy. After 4 h stirring, the remaining metal was filtered off and the concentration of $Ph_3CK$/THF solution was determined by titration of acetanilide as 0.146 mol/l.

The methyl methacrylate was purified by introduction of nitrogen and storage over alumina, followed by stirring over $CaH_2$ and subsequent recondensation under reduced pressure.

The (1-naphthyl)$Ph_3PBr$ was first dried for about 8h at about 100° C. in a high vacuum. The (1-naphthyl)$Ph_3PBr$ thus predried was then slurried up in the THF and titrated with tritylpotassium/THF solution at room temperature to a red color. The white (1-napthyl)$Ph_3PBr$ was then filtered off and subsequently dried under reduced pressure.

I. Initiator preparation

The initiator was prepared by adding a stoichiometric amount of (1-naphthyl) (phenyl)$_3P^+Br^-$ (=NTPBr) to tritylpotassium in THF (50 ml) at room temperature to afford a 0.004 mol/l, red initiator solution.

II. Polymerization 1) 0.8 g methylmethacrylate (MMA) in THF (7 ml) were added dropwise at room temperature to a 0.004 mol/l initiator solution in THF (50 ml), prepared as described above. After stirring for 0.5h at room temperature and 21.7 h at 70° C. the polymerization was quenched by addition of methanol/acetic acid (10/1) and the polymer isolated by precipitation in methanol followed by filtration and drying to constant weight in a vacuum oven at 50° C. The weight of the isolated white polymethylmethacrylate powder corresponded to a yield of 100%.

2) 0.8 g MMA in THF (7 ml) were added dropwise at 70° C. to a 0.004 mol/l initiator solution in THF (50 ml), prepared as described above. After 21.5 h at 70° C. the polymerization was quenched by addition of methanol/acetic acid (10/1) and the polymer isolated by precipitation in methanol followed by filtration and drying to constant weight in a vacuum oven at 50° C. The weight of the isolated white polymethylmethacrylate powder corresponded to a yield of 98%.

After specified intervalls small aliquots were taken from the polymerization mixture and quenched by addition of methanol/acetic acid (10/1). The number average molecular weight $M_n$ and the ratio of weight average molecular weight to number average molecular weight $M_w/M_n$ of the samples obtained were determined by size exclusion chromatography (SEC) relative to polymethylmethacrylate standards.

The results of the examples 1) and 2) are documented in the following table.

TABLE

| | Example 1) | | Example 2) | |
|---|---|---|---|---|
| t/min[a)] | $M_n$ (g/mol) | $M_w/M_n$ | $M_n$ (g/mol) | $M_w/M_n$ |
| 6 | 1700 | 1.05 | 1600 | 1.05 |
| 19 | 2500 | 1.03 | | |
| 49 | 3800 | 1.11 | | |
| 130 | | | 14500 | 1.07 |
| 180 | 9300 | 1.17 | | |
| 1290 | | | 17300 | 1.09 |
| 1300 | 19000 | 1.18 | | | a) reaction time at a temperature of 70° C.

What is claimed is:

1. A method for preparing a (co)polymer having an average $M_w/M_n \leq 1.2$, comprising the steps of:

mixing a monomer of the formula I, or a monomer of the formula II, or a mixture of both I and II:

$$\begin{array}{c} R^1 \quad R^2 \\ \diagdown \, \diagup \\ C \\ \| \\ CH_2 \end{array} \quad (I)$$

-continued

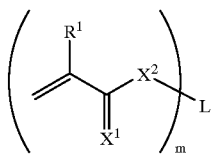
(II)

with an initiator corresponding to or containing $$((R^6R^7R^8PR^9)^+)_n\ Q^{n-}\ \text{(III) and/or } (R^6R^7R^8PR^9)^+(Q')^- \quad \text{(IV)}$$

and conducting the reaction at temperature of from 50° C. to 150° C., in the presence or the absence of a solvent, for a length of time sufficient to polymerize the monomer(s) to form a (co)polymer; and isolating the formed (co)polymer, wherein $R^1$ is selected from the group consisting of CN, methyl and phenyl, $R^2$ is independently selected from the group consisting of CN and $C(=O)R^3$, $X^1$ is O, $R^3$ is alkyl of from 1 to 20 carbon atoms, substituted alkyl of from 1 to 20 carbon atoms, having as substituents one or more halides, —O-alkyl of from 1 to 20 carbon atoms, substituted —O-alkyl of from 1 to 20 carbon atoms having as substituents one or more halides, —O-alkyl of from 3 to 20 carbon atoms having one or more epoxy units, —O-cycloalkyl of from 3 to 15 carbon atoms, —O-cycloalkyl of from 3 to 15 carbon atoms having as substituents one or more halides, —O-cycloalklyl of from 5 to 12 carbon atoms having one or more epoxy units, —O-alkenyl of from 2 to 12 carbon atoms, —O—R'—O—R" or —O—R'—NR"R''', wherein R' is an alkylene chain of from 2 to 10 carbon atoms, $C_6$- to $C_{18}$-arylene, an alkylene chain having one or more ether units in the chain, R" is $C_1$- to $C_{10}$-alkyl, $C_6$- to $C_{18}$-aryl, $C_3$- to $C_{10}$-cycloalkyl, or $C_3$- to $C_{30}$-organosilyl and R''' is H, $C_1$- to $C_{10}$-alkyl, $C_6$- to $C_{18}$-aryl, $C_3$- to $C_{10}$-cycloalkyl, $C_3$- to $C_{30}$-organosilyl, or —S-alkyl of from 1 to 20 carbon atoms;

$X^2$ is 0;

L is an alkylene of from 1 to 16 carbon atoms, or an arylene of from 6 to 18 carbon atoms, which may be substituted with m functional groups $CH_2=C(R^1)C(=O)O-$ m is an integer of from 2 to 20;

$R^6$ $R^7$ and $R^8$ are independently $C_6$- to $C_{14}$-aryl or substituted $C_6$- to $C_{14}$-aryl having one or more substituents selected from the group consisting of alkyl of from 1 to 16 carbon atoms, oxyalkyl of from 1 to 16 carbon atoms, $C_6$- to $C_{14}$-aryl, oxy-$C_6$- to $C_{14}$-aryl, substituted oxy-6- to $C_{14}$-aryl, alkylene-oxy-alkyl of from 3 to 17 carbon atoms, aminodialkyl of from 2 to 14 carbon atoms, amino(alkyl) (aryl) (aryl) of from 7 to 15 carbon atoms, aminodiaryl of from 12 to 28 carbon atoms, halides, thio-alkyl of from 1 to 16 carbon atoms, and substitute thio-$C_6$- to $C_{14}$-aryl, $R^9$ is 1-naphthyl, 2-naphthyl, 1-anthracenyl, 2-anthracenyl, 9-anthracenyl, 1-phenanthryl, 2-phenanthryl, 3-phenanthryl, 4-phenanthryl or 9-phenanthryl, said naphthyl, anthracenyl or phenanthryl having one or more substituents selected from the group consisting of halides, alkyl of from 1 to 20 carbon atoms, oxyalkyl of from 1 to 20 carbon atoms, $C_6$- to $C_{22}$-aryl, substituted $C_6$- to $C_{22}$-aryl, oxy-aryl of from 6 to 18 carbon atoms, substituted oxyalkyl of from 6 to 20 carbon atoms, aminodialkyl having from 2 to 30 carbon atoms, amino(alkyl)(aryl) having from 7 to 30 carbon atoms, aminodiaryl of from 12 to 36 carbon atoms, thio-alkyl of from 1 to 20 carbon atoms, thio-$C_6$- to $C_{22}$-aryl, and substituted thio-$C_6$- to $C_{22}$-aryl, Q is $CR^{10}R^{11}R^{12}$, $NR^{13}R^{14}$, $OR^{15}$, $SR^{16}$ or $R^{17}(CR^{10}R^{11})_p(NR^{13})_q(O)_r(S)_s$ wherein p, q, r and s are independently an integer of from 0 to 30 and where the sum of p to s is at least 2;

Q' is $R^{18}$—$CR^{10}R^{11}R^{12}$, $R^{18}$—$NR^{13}R^{14}$, $R^{18}$—$OR^{15}$, $R^{18}$—$SR^{16}$, $R^{18}$—Z;

$R^{10}$ and $R^{11}$ are independently alkyl, each of from 1 to 10 carbon atoms, alkyl of from 1 to 10 carbon atoms having as substituents one or more halides, $C_6$- to $C_{14}$-aryl, substituted $C_6$- to $C_{14}$-aryl, CN, $C(=O)R^3$ as defined above, organosilyl having from 3 to 18 carbon atoms, or either $R^{10}$ or $R^{11}$ are H, or $R^{10}$ and $R^{11}$ are joined together to form a ring, having from 3 to 10 carbon atoms, $R^{12}$ is H, alkyl of from 1 to 10 carbon atoms, $C_6$- to $C_{14}$-aryl, or a (co)polymer radical;

$R^{13}$ and $R^{14}$ are independently alkyl of from 1 to 10 carbon atoms, $C_6$- to $C_{14}$-aryl, $C_7$- to $C_{15}$ aralkyl, $C_3$- to $C_{18}$-organosilyl, or $R^{13}$ and $R^{14}$ are joined together to form a heterocycle, $R^{15}$ and $R^{16}$ are independently alkyl of from 1 to 10 carbon atoms, cycloalkyl of from 3 to 10 carbon atoms or $C_6$- to $C_{14}$-aryl, $R^{17}$ is an alkylene of from 2 to 10 carbon atoms, cycloalkylene of from 3 to 10 carbon atoms, or an $C_6$- to $C_{10}$-arylene, $R^{18}$ is a (co)polymer radical;

Z is a radical derived from an initiator for the anionic polymerization of anionic polymerizable monomers other than radicals derived from compound Ill or IV, n is an integer of from 1 to 30.

2. The method of claim 1, wherein $R^6$ to $R^8$ are phenyl.

3. The method of claim 1, wherein said initiator corresponds to or contains

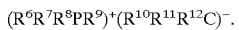
$(R^6R^7R^8PR^9)^+(R^{10}R^{11}R^{12}C)^-$.

4. The method of claim 1, wherein said initiator corresponds to or contains

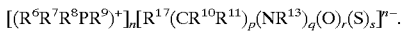
$[(R^6R^7R^8PR^9)^+]_n[R^{17}(CR^{10}R^{11})_p(NR^{13})_q(O)_r(S)_s]^{n-}$.

5. The method of claim 1, wherein said monomer I is a (meth)acrylate ester of a $C_1$- to $C_{20}$-alcohol, acrylonitrile, a cyanoacrylate ester of a $C_1$- to $C_{20}$-alcohol, a vinyl heterocycle selected from the group consisting of vinyl pyridines and vinyl pyrimidines.

6. The method of claim 1, wherein said monomer II is a methacrylate di- or polyester of an aliphatic or aromatic di- or polyalcohol.

7. The method of claim 5, wherein said monomer I is selected from the group consisting of methyl methacrylate, n-butyl methacrylate, t-butyl methacrylate, 2-ethylhexyl methacrylate, allyl methacrylate and lauryl methacrylate.

8. The method of claim 1, wherein the reaction is carried out in the absence of a solvent.

9. The method of claim 1, wherein the reaction is carried out in the presence of a solvent in which the initiator at least partially dissolves and which does not quench the reaction.

10. The method of claim 9 wherein as solvent ether, cyclic ether, aromatic hydrocarbons or mixtures thereof are used.

11. The method of claim 1 wherein as part of the isolating step the reaction mixture is quenched with an acyl halide, an acid anhydride or a substance containing an active hydrogen atom prior to isolating the formed (co)polymer.

* * * * *

Disclaimer 6,143,847—Thieo E. Hogan-Esch, South Pasadena; Dimo K. Dimov, Los Angeles, both of Calif.; Stephan Jungling, Mannheim, Germany; Volker Warzelhan, Weisenheim, Germany; Hermann Gausepohl, Mutterstadt, Germany. METHOD FOR PREPARING (CO) POLYMERS BY METAL-FREE ANIONIC POLYMERIZATION IN THE PRESENCE OF A PHOSPHONIUM CATION CONTAINING AT LEAST ONE ANNELLATED AROMATIC RING. Patent dated November 7, 2000. Disclaimer filed May 10, 2001 by the assignee, BASF Aktiengesellschaft.

Hereby enter this disclaimer to the remaining term of said patent.
*(Official Gazette, August 27, 2002)*